US012419847B2

(12) United States Patent
Chang et al.

(10) Patent No.: US 12,419,847 B2
(45) Date of Patent: Sep. 23, 2025

(54) COMPOSITION AND METHOD FOR ATTENUATING NEUROINFLAMMATION, AMYLOIDOPATHY AND TAUOPATHY

(71) Applicant: Trustees of Dartmouth College, Hanover, NH (US)

(72) Inventors: Ta Yuan Chang, Etna, NH (US); Catherine C.Y. Chang, Etna, NH (US); Haibo Li, Hanover, NH (US); Adrianna De La Torre, Lyme, NH (US); Thao N. Huynh, Concord, NH (US)

(73) Assignee: Trustees of Dartmouth College, Hanover, NH (US)

( * ) Notice: Subject to any disclaimer, the term of this patent is extended or adjusted under 35 U.S.C. 154(b) by 733 days.

(21) Appl. No.: 17/722,629

(22) Filed: Apr. 18, 2022

(65) Prior Publication Data

US 2022/0257544 A1    Aug. 18, 2022

Related U.S. Application Data

(63) Continuation-in-part of application No. PCT/US2021/057570, filed on Nov. 1, 2021.

(60) Provisional application No. 63/118,216, filed on Nov. 25, 2020.

(51) Int. Cl.
*A61K 31/167* (2006.01)
*A61K 9/127* (2006.01)
*A61P 25/28* (2006.01)

(52) U.S. Cl.
CPC ............ *A61K 31/167* (2013.01); *A61K 9/127* (2013.01); *A61P 25/28* (2018.01)

(58) Field of Classification Search
CPC ........ A61K 31/167; A61K 9/127; A61P 25/28
See application file for complete search history.

(56) References Cited

U.S. PATENT DOCUMENTS

| | | | |
|---|---|---|---|
| 8,466,121 B2 | 6/2013 | Chang et al. | |
| 8,802,646 B2 | 8/2014 | Chang et al. | |
| 9,149,492 B2 | 10/2015 | Chang et al. | |
| 9,388,413 B2 * | 7/2016 | Chang | A61K 31/70 |
| 9,388,414 B2 | 7/2016 | Chang et al. | |
| 2006/0135785 A1 | 6/2006 | Patoiseau et al. | |
| 2016/0206615 A1 * | 7/2016 | Tangutoori | A61K 9/1272 |

OTHER PUBLICATIONS

Chang et al, Cellular Cholesterol Homeostasis and Alzheimer's Disease, Journal of Lipid Research, vol. 58, pp. 2239-2254. (Year: 2017).*

Aytan et al. (2013) "Combination Therapy in a Transgenic Model of Alzheimer's Disease," Exp. Neurol. 250:228-238.

(Continued)

*Primary Examiner* — Carlos A Azpuru
(74) *Attorney, Agent, or Firm* — Licata & Tyrrell P.C.; Jane Massey Licata

(57) ABSTRACT

The present invention features compositions and methods for preventing or treating neuroinflammation, amyloidopathy or tauopathy by inhibiting Acyl-CoA:Cholesterol Acyltransferase activity, in particular with brain-permeable inhibitors encapsulated in a stealth liposome-based nanoparticle. Stealth liposome-based nanoparticles for reducing or attenuating amyloidopathy or tauopathy are also provided.

6 Claims, 10 Drawing Sheets

Specification includes a Sequence Listing.

(56) References Cited

OTHER PUBLICATIONS

Chang et al. (2017) "Cellular Cholesterol Homeostasis and Alzheimer's Disease," J. Lipid Res. 58(12):2239-2254.
Hutter-Paier et al. (2004) "The ACAT Inhibitor CP-113,818 Markedly Reduces Amyloid Pathology in a Mouse Model of Alzheimer's Disease," Neuron 44:227-238.
International Search Report and Written Opinion in PCT/US2021/057570 dated Jan. 27, 2022.

* cited by examiner

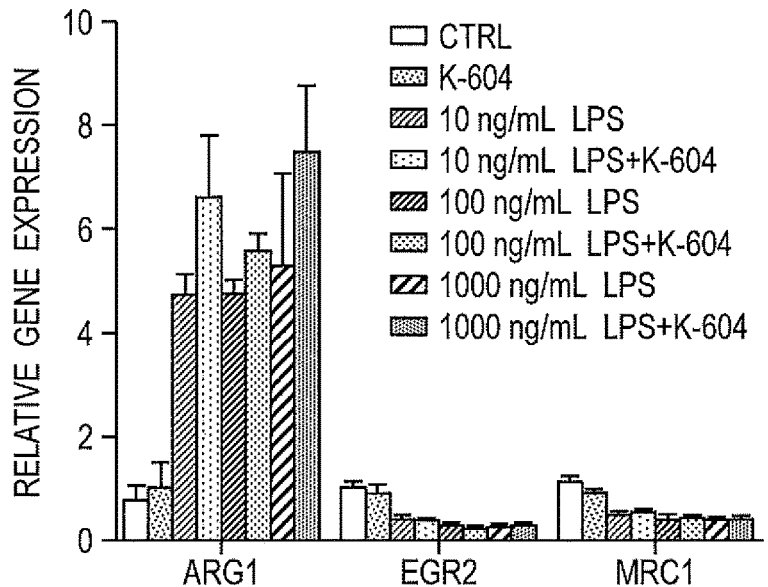
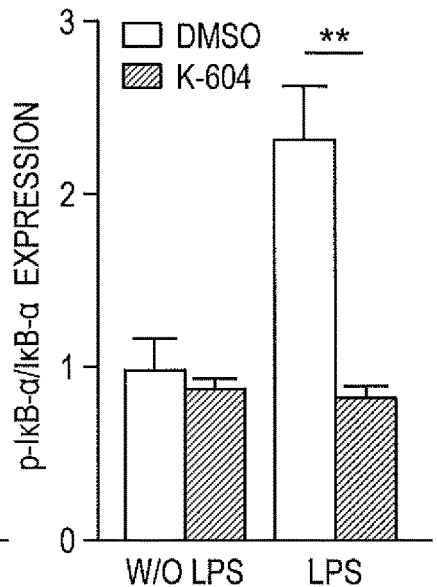
FIG. 4B    FIG. 4C
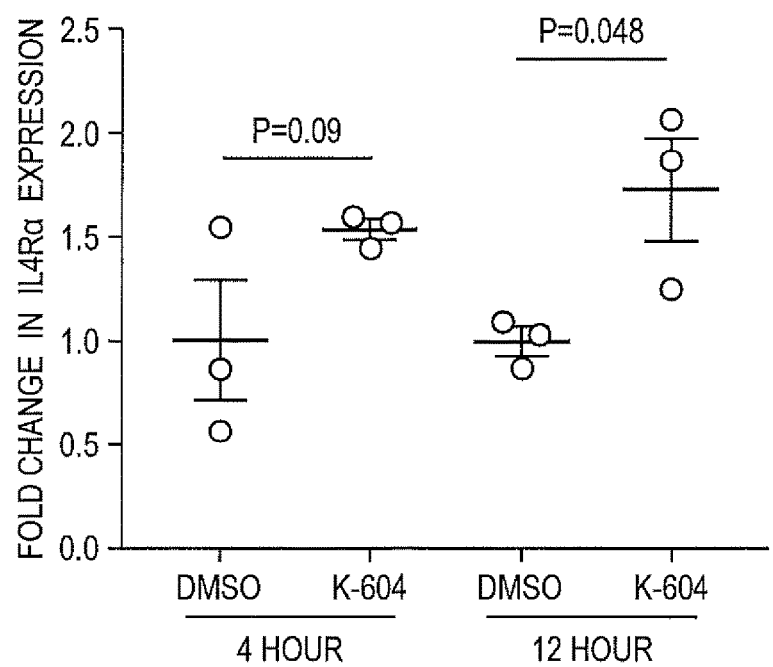
FIG. 5

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ggagctgaag ccactattta t                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
ctgtttgaag tggaccacat ca                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
cccggttcat tctgatactg ga                                             22

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
aactacccaa ggactcctac tgta                                           24

<210> SEQ ID NO 5
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 5
tgctgtccag tatcagaatg aaccgggttt tggccactga ctgacccggt tcactgatac    60
tgga                                                                 64
```

```
<210> SEQ ID NO 6
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 6
tgctgtacag taggagtcct tgggtagttt tggccactga ctgactaccc aagctcctac    60
tgta                                                                64

<210> SEQ ID NO 7
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 7
caugaucuuc cagauuggag uucua                                         25

<210> SEQ ID NO 8
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 8
uagaacucca aucuggaaga ucaug                                         25

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 9
tactgcgcgt ggagacg                                                  17
```

COMPOSITION AND METHOD FOR ATTENUATING NEUROINFLAMMATION, AMYLOIDOPATHY AND TAUOPATHY

INTRODUCTION

This application is a continuation-in-part application of PCT/US2021/057570, filed Nov. 1, 2021, which claims the benefit of priority of U.S. Provisional Application No. 63/118,216, filed Nov. 25, 2020, the content of which is incorporated herein by reference in its entirety.

This invention was made with government support under Grant Numbers AG037609 and AG063544 awarded by the National Institutes of Health. The government has certain rights in the invention.

BACKGROUND

Chronic neuroinflammation is a hallmark of late onset Alzheimer's disease (LOAD) and in many other neurodegenerative diseases, as well as in aging. In the central nervous system (CNS), the Toll-Like Receptor 4 (TLR4) is expressed in microglia, astrocytes, oligodendrocytes, and neurons. It is a transmembrane receptor protein that recognizes diverse pathogen-derived ligands including lipopolysaccharides (LPS), and various tissue damage-related ligands including oligomeric amyloid peptide fragment A1$\beta$1-42, heat-shock proteins (especially HSP60 and HSP70), high mobility group box 1 (HMGB1), hyaluronic acid, fibronectin, galectin-3, and the like. TLR4 is a LOAD susceptibility gene. In LOAD, aging, and several neurodegenerative diseases, TLR4 plays a key role in mediating pro-inflammatory responses, such as pro-inflammatory cytokine production in the CNS, when bound to various ligands including LPS.

Cholesterol is stored as cholesteryl esters. For cholesterol esterification, there are two Acyl-CoA:Cholesterol Acyltransferase (ACAT) genes, SOAT1 and SOAT2, encoding two homologous but distinct enzymes, ACAT1 and ACAT2. Both enzymes use long-chain fatty acyl-CoAs and sterols with 3-beta-OH, including cholesterol and various oxysterols as their substrates. ACAT1 is the major cholesterol storage enzyme in the brain. Both compound K-604 (Ki=0.5 $\mu$M) and compound F12511 (Ki=0.04 $\mu$M) are high-affinity, ACAT1-specific, small-molecule inhibitors. Both inhibitors had passed phase I clinical safety tests for treating cardiovascular disease. K-604 is rather hydrophilic, while F12511 is extremely hydrophobic and both inhibitors tightly bind to ACAT1. F12511 preferentially inhibits ACAT1 but it also inhibits ACAT2 (Ki=0.11 $\mu$M).

Using a custom-made slow-release pellet method, the isoform-non-specific ACAT inhibitor CP113,818 has been shown to reduce amyloidopathy and rescue cognitive deficits in a mouse model for Alzheimer's Disease (AD) (Hutter-Paier, et al. (2004) Neuron 44(2):227-38). Similarly, the isoform-non-specific ACAT inhibitor, CI 1011, has been shown to reduce amyloidopathy in a mouse model for AD. In this respect, a method for preparing a water-soluble formulation containing CI 1011 has been described, wherein CI 1011 is incorporated with albumin such that CI 1011 can achieve relatively high concentration in the blood (Lee, et al. (2015) ACS Nano 9(3):2420-32). However, it has not been shown that CI 1011 is able to enter the brain using such a formulation.

SUMMARY OF THE INVENTION

The present invention features compositions and methods for reducing or attenuating neuroinflammation, amyloidopathy and/or tauopathy. Compositions of this invention include nanoparticles having a core and an outer lipid envelope, wherein the core includes an Acyl-CoA:Cholesterol Acyltransferase (ACAT) inhibitor and the outer lipid envelope comprises or consists of distearoyl-sn-glycero-3-phosphoethanolamine-poly(ethylene glycol) (DSPE-PEG) and phosphatidylcholine (PC), wherein the concentration of phosphatidylcholine is greater than or equal to 6 mM. In some aspects, the ACAT inhibitor is F12511 or an analog thereof (e.g., Analogs 1, 2, 2c, or 3 (F26)). In other aspects, the ratio of ACAT inhibitor to PC is in the range of about 0.3:1 to 2:1. In further aspects, the invention provides empty DSPE-PEG/PC nanoparticles (i.e., no ACAT inhibitor) for reducing or attenuating amyloidopathy and/or tauopathy. A pharmaceutical composition including the above-referenced nanoparticles in admixture with a pharmaceutically acceptable carrier is also provided, wherein said composition is preferably formulated for intravenous or intraperitoneal delivery. This invention further provides methods of administering the above-referenced nanoparticle compositions to a subject to reduce or attenuate neuroinflammation, amyloidopathy and/or tauopathy in the subject, wherein the nanoparticles encapsulating an ACAT inhibitor maintain a concentration of the ACAT inhibitor in the blood of the subject at above 20 $\mu$M for at least 4 hours. In some aspects, the method further includes the administration of a second therapeutic agent, e.g., a $\beta$-secretase inhibitor, $\gamma$-secretase modulator, proteasome inhibitor, small molecule activator of the unfolded protein response, Hsp90 inhibitor, small molecule Hsc70 inhibitor, deubiquitination enzyme inhibitor, epigallocatechin-3-gallate, variant of Hsp104 disaggregase, glutathione ethyl ester or antibody.

BRIEF DESCRIPTION OF THE DRAWINGS

FIG. 4A-4C show that inhibiting ACAT1 in N9 microglial cells attenuates inflammatory responses to LPS. Cells were seeded at 1×10$^5$/well onto 12-well plates in RPMI-1640 with 10% bovine calf serum. FIG. 4A and FIG. 4B, Cells were treated with DMSO (control) or DMSO with 0.5 µM Acat1 inhibitor K-604 for 4 hours, then treated without or with 10, 100, or 1000 ng/mL LPS. Six hours later, mRNA was extracted, and qPCR was performed to monitor pro-inflammatory (FIG. 4A) or anti-inflammatory (FIG. 4B) gene expression. FIG. 4C, N9 cells were treated with DMSO (control) or DMSO with 0.5 µM K-604 for 4 hours then treated without or with 100 ng/mL LPS. Thirty minutes later, proteins were extracted for western blot analysis for total IκB-α, and for phosphorylated IκB-α (p-IκB-α). *P<0.05; ** P<0.01.

FIG. 5 shows that inhibiting ACAT1 in microglial N9 cells increases expression of the receptor IL-4Rα (the key receptor for the anti-inflammatory cytokine IL4). Microglial N9 cells grown in RPMI including 10% bovine calf serum were treated with DMSO without or with the ACAT1 inhibitor K-604 at 0.5 µM for 4 or 12 hours as indicated. Cells were harvested for immunoblot analysis for IL-4Rα. Vinculin was the loading control. Data expressed as mean+/− SEM, * p<0.05, ** p<0.01.

DETAILED DESCRIPTION OF THE INVENTION

Figure 1A:
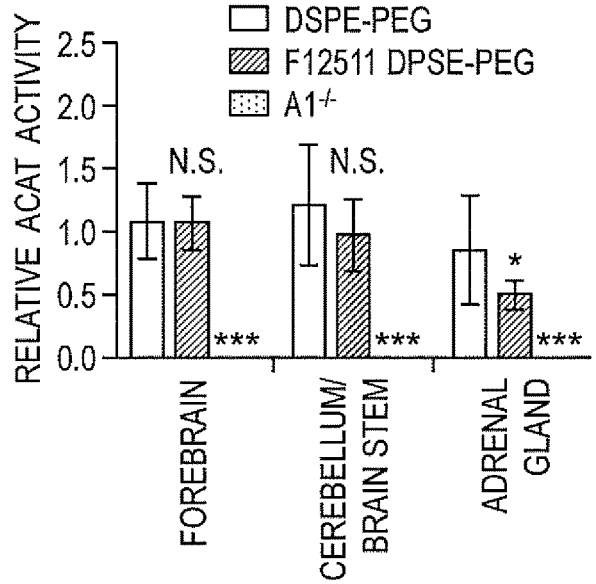
FIG. 1A-1D show that IV injection of nanoparticle F12511 reduces ACAT activity in both adrenal glands and cerebellum, while nanoparticle K-604 tends to reduce ACAT activity in adrenal glands but not in brain. This result demonstrates that when delivered by IV, F12511 is permeable to the brain while K-604 is not. WT mice were IV injected with nanoparticle F12511 (30 mM DSPE-PEG with 5 mol % F12511; 5.8 mg/kg) or with DSPE-PEG vehicle and sacrificed after 1 hour (FIG. 1A), 4 hours (FIG. 1B), or 8 hours (FIG. 1C). WT mice were IV injected with nanoparticle K-604 (30 mM DSPE-PEG with 40 mol % K-604) or with vehicle and sacrificed after 4 hours (FIG. 1D). A1$^{-/-}$ refers to Acat1$^{-/-}$ mouse. ACAT activity was determined by using a mixed liposome assay. N=4 for WT mice age (2-3 months) and gender matched. N=1 for A1$^{-/-}$ mouse. N.S., not significant; P<0.05*, P<0.01, P<0.001*. Analysis by two-way ANOVA. The significance is relative to vehicle-treated group.

This invention provides stealth nanoparticles encapsulating an Acyl-CoA:Cholesterol Acyltransferase (ACAT) inhibitor for reducing or attenuating neuroinflammation, amyloidopathy and/or tauopathy. In particular, stealth nanoparticles composed of distearoyl-sn-glycero-3-phosphoethanolamine-poly(ethylene glycol) and phosphatidylcholine, when delivered by intravenous injection or by intraperitoneal injection at 30 mM, provide a concentration of the ACAT inhibitor in the blood of a subject at above 20 μM for at least 4 hours thereby effectively allowing for delivery of the ACAT inhibitor into brain cells. ACAT1 blockage attenuates LPS-mediated inflammatory responses by diminishing the TLR4-mediated pro-inflammatory signaling cascade and inhibits cholesterol esterification in neuronal and microglial cell lines, without being toxic to said cells. Moreover, the incorporation of at least 6 mM phosphatidylcholine in the nanoparticle envelope provides for encapsulation of high concentrations of hydrophobic compounds. Notably, a significant portion of the stealth nanoparticle by itself can enter the brain interior and, whether empty or encapsulating an ACAT inhibitor, can reduce hyperphosphorylated and aggregated htau and reduce amyloid burden. Accordingly, the present invention provides stealth nanoparticle compositions and methods for reducing or attenuating neuroinflammation, amyloidopathy and/or tauopathy resulting from pro-inflammatory responses it the CNS and preventing or treating LOAD as well as other related neurodegenerative diseases such as vascular dementia, tauopathy, Parkinson's disease, frontotemporal dementia, amyotrophic lateral sclerosis, and adult glioma by inhibiting ACAT1 encapsulated in a stealth nanoparticle.

A nanoparticle of this invention denotes a sphere with a mean diameter of less than 300 nm, which has a circular, unilamellar lipid wall or envelop and a central component or core that contains one or more ACAT inhibitors, and optionally one or more additional therapeutic ingredients. The nanoparticles of this invention are "stealth" in that they have the ability to not be detected and then sequestered and/or degraded, or to be hardly detected and then sequestered and/or degraded, and/or to be detected and then sequestered and/or degraded late, by the immune system of the host to which they are administered. In this respect, the nanoparticles exhibit long circulating properties which provide them with a half-life time in the blood compartment of greater than 2, 4, 6, 8, 10, or 12 hours thereby making it possible to allow a significant portion of the nanoparticle (approximately 0.5% (Saucier-Sawyer et al. (2015) J. Drug Target. 23(7-8):736-49) to enter the brain. Once in the brain, a nanoparticle composed of DSPE-PEG and PC can exert various biological effects on various cell types in the CNS (e.g., reduce hyperphosphorylated and aggregated htau and reduce amyloid burden). Further, the nanoparticles according to the present invention can carry a relatively high content of active ingredient through a subject thereby providing reduced toxicity compared with free drug in solution.

In certain aspects, the nanoparticles of this invention have at least one dimension in the range of about 10 nm to about 300 nm, including any integer value between 1 nm and 300 nm (including about 20, 30, 40, 50, 60, 70, 80, 90, 100, 200, 250, and 300). In certain aspects, the nanoparticles have at least one dimension that is about 15 nm to 250 nm. Particle size can be determined using any method known in the art, including, but not limited to, sedimentation field flow fractionation, photon correlation spectroscopy, disk centrifugation, dynamic light scattering, and electron microscopy.

The stealth nanoparticles which are the subject of the present invention are composed of a core which is liquid or semi-liquid at ambient temperature, and an lipid envelope composed of phosphatidylcholine (PC) and a biodegradable phospholipid, preferably a pegylated phospholipid, most preferably distearoyl-sn-glycero-3-phosphoethanolamine-poly(ethylene glycol)$_x$ (DSPE-PEG$_x$), in which x represents the size of the PEG molecule in g/mol. In some aspects, the molar mass of the PEG component is in the range of about 100 to about 20,000 g/mol, including about 500 g/mol, about 600 g/mol, about 700 g/mol, about 800 g/mol, about 900 g/mol, about 1000 g/mol, about 2000 g/mol, about 3000 g/mol, about 5000 g/mol, about 10,000 g/mol, about 15,000 g/mol, and about 20,000 g/mol. In certain aspects, the molar mass of the PEG component is greater than or equal to 1000 g/mol, preferably greater than or equal to 2000 g/mol. In some aspects, DSPE-PEG$_{1000}$, DSPE-PEG$_{2000}$, DSPE-PEG$_{3000}$ or DSPE-PEG$_{5000}$ is used. In particular aspects, DSPE-PEG$_{2000}$ or DSPE-PEG$_{5000}$ is used. Preferably, the nanoparticles include between 20 mM and 40 mM, preferably between 25 mM and 35 mM, most preferably 30 mM of the pegylated phospholipid (e.g., DSPE-PEG$_{2000}$ or DSPE-PEG$_{5000}$).

Ideally, the phosphatidylcholine used in the preparation of the nanoparticles is purified to at least 95%, 96%, 97%, 98%, 99% or 100% homogeneity. In this respect, the phosphatidylcholine has less than 5%, 4%, 3%, 2%, 1%, 0.5%, or 0.1% impurities such as other phosphatides (e.g., phosphatidylethanolamine, phosphatidylserine, phosphatidic acid, and phosphatidylinositol), triglycerides, fatty acids, or carbohydrates: In particular aspects, the nanoparticles include between 2 mM and 10 mM, preferably between 4 mM and 8 mM, most preferably 6 mM phosphatidylcholine.

As used herein, an "inhibitor of ACAT1" or "ACAT1 inhibitor" is any molecular species that is an inhibitor of the ACAT1 enzyme, which may or may not also inhibit ACAT2. Methods for assessing the selectively of ACAT1 inhibitors are known in the art and can be based upon any conventional assay including, but not limited to the determination of the half maximal (50%) inhibitory concentration (IC) of a substance (i.e., 50% IC, or IC$_{50}$), the binding affinity of the inhibitor (i.e., K$_i$), and/or the half maximal effective concentration (EC$_{50}$) of the inhibitor for ACAT1 as compared to ACAT2. See, e.g., Lada, et al. (2004) J. Lipid Res. 45:378-386 and U.S. Pat. No. 5,968,749. ACAT1 and ACAT2 proteins that can be used in such assays are well-known in the art and set forth, e.g., in GENBANK Accession Nos. NP 000010 (human ACAT1) and NP 005882 (human ACAT2). See also U.S. Pat. No. 5,834,283.

Ideally, the inhibitor is brain-permeable. The term "brain-permeable" refers to the ability of a drug to cross the blood brain barrier. In some aspects, animal pharmacokinetic (pK) studies, such as mouse pharmacokinetic/blood-brain barrier studies, can be used to determine or predict brain permeability. For example, various concentrations of a compound or pharmaceutical composition containing the same can be administered and various pK properties are measured in an animal model. In particular, dose-related plasma and brain levels are determined. In some aspects, good brain penetration is about 0.1%, 1%, more than 5%, or more than about 10% of the dose that crosses the blood brain barrier after a given period of time.

In particular aspects, ACAT1 inhibitors are agents that exhibit an $IC_{50}$ value for ACAT1 that is at least twice or, more desirably, at least three, four, five, or six times higher than the corresponding $IC_{50}$ value for ACAT2. Most desirably, an ACAT1 inhibitor has an $IC_{50}$ value for ACAT1 which is at least one order of magnitude or at least two orders of magnitude higher than the $IC_{50}$ value for ACAT2.

Inhibitors of ACAT1 activity have been described. See, e.g., inhibitors listed in Table 1. For example, Ikenoya, et al. ((2007) Atherosclerosis 191:290-297) teach that K-604 has an $IC_{50}$ value of 0.45 μmol/L for human ACAT1 and 102.85 μmol/L for human ACAT2. As such K-604 is 229-fold more selective for ACAT1 than ACAT2. In addition, diethyl pyrocarbonate has been shown to inhibit ACAT1 with 4-fold greater activity ($IC_{50}$=44 μM) compared to ACAT2 ($IC_{50}$=170 μM) (Cho, et al. (2003) Biochem. Biophys. Res. Comm. 309:864-872). Ohshiro, et al. ((2007) J. Antibiotics 60:43-51) teach selective inhibition with beauveriolides I (0.6 μM vs. 20 μM) and III (0.9 μM vs. >20 μM) for ACAT1 over ACAT2. In addition, beauveriolide analogues 258, 280, 274, 285, and 301 show ACAT1 inhibition with $pIC_{50}$ values in the range of 6 to 7 (Tomoda & Doi (2008) Accounts Chem. Res. 41:32-39). Lada, et al. ((2004) J. Lipid Res. 45:378-386) teach a Warner-Lambert compound (designated therein as Compound 1A), and derivatives thereof (designated Compounds 1B, 1C, and 1D), which inhibit ACAT1 more efficiently than ACAT2 with $IC_{50}$ values 66- to 187-fold lower for ACAT1 than for ACAT2 (see Table 1). Moreover, Lee, et al. ((2004) Bioorg. Med. Chem. Lett. 14:3109-3112) teach methanol extracts of *Saururus chinensis* root that contain saucerneol B and manassantin B for inhibiting ACAT activity. Saucerneol B inhibited hACAT-1 and hACAT-2 with $IC_{50}$ values of 43 and 124 μM, respectively, whereas manassantin B inhibited hACAT-1 and hACAT-2 with $IC_{50}$ values of 82 μM and only 32% inhibition at 1 mM, respectively.

TABLE 1

| Inhibitor | Structure | $IC_{50}$ ACAT1 | $IC_{50}$ ACAT2 |
| --- | --- | --- | --- |
| K-604 | 2-[4-[2-(benzimidazol-2-ylthio)ethyl]piperazin-1yl]-N-[2,4-bis(methylthio)-6-methyl-3-pyridyl]acetamide | 0.45 μmol/L | 103 μmol/L |
| Beauveriolide I | 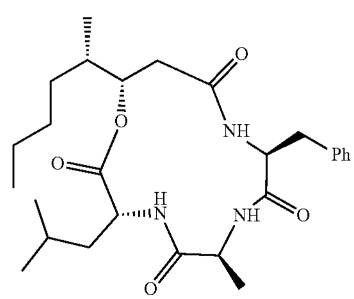 [SMILES: CCCC[C@H](C)[C@@H]1CC(=O)N[C@@H](Cc2ccccc2)C(=O)N[C@@H](C)C(=O)N[C@H](CC(C)C)C(=O)O1] | 0.6 μM | 20 μM |
| Beauveriolide III | 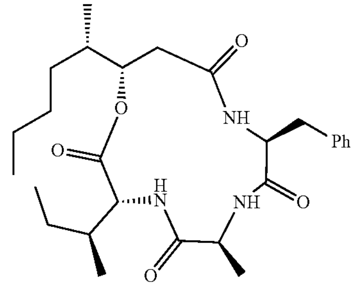 [SMILES: CCCC[C@H](C)[C@@H]1CC(=O)N[C@@H](Cc2ccccc2)C(=O)N[C@@H](C)C(=O)N[C@H]([C@@H](C)CC)C(=O)O1] | 0.9 μM | >20 μM |

TABLE 1-continued

| Inhibitor | Structure | IC$_{50}$ ACAT1 | IC$_{50}$ ACAT2 |
|---|---|---|---|
| Eflucimibe (F12511) | 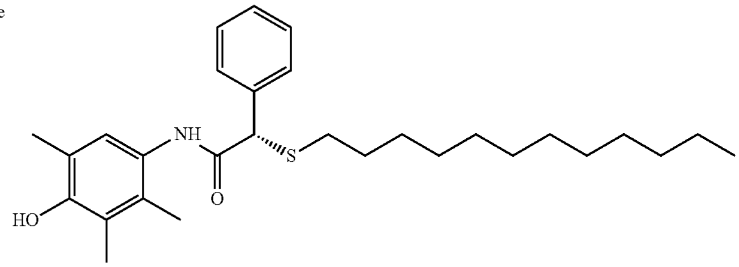 | 39 nM | 110 nM |
| Compound 1A | 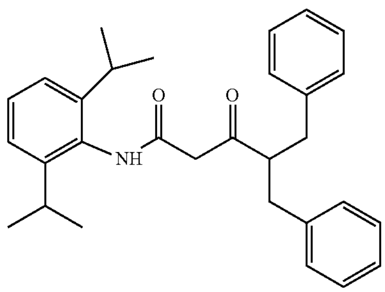 [SMILES: CC(C)c1cccc(C(C)C)c1NC(=O)CC(=O)C(Cc1ccccc1)Cc1ccccc1] | 4.2 nM | 275 nM |
| Compound 1B | 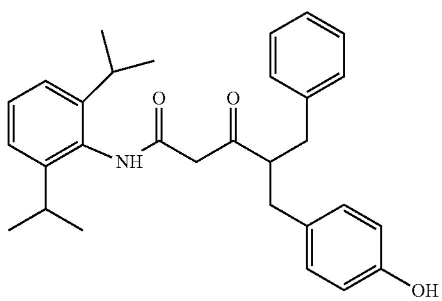 [SMILES: CC(C)c1cccc(C(C)C)c1NC(=O)CC(=O)C(Cc1ccccc1)Cc1ccc(O)cc1] | 10.3 nM | 1500 nM |
| Compound 1C | 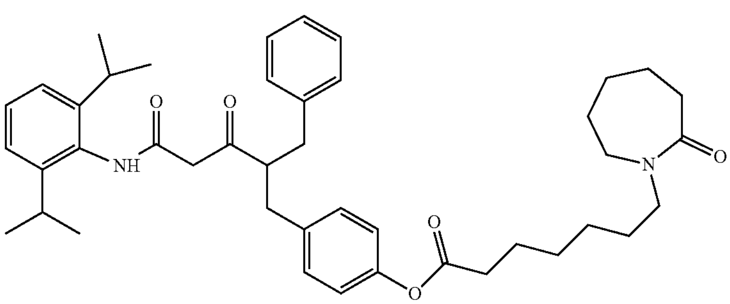 [SMILES: CC(C)c1cccc(C(C)C)c1NC(=O)CC(=O)C(Cc1ccccc1)Cc1ccc(OC(=O)CCCCCCN2CCCCCC2=O)cc1] | 3.6 nM | 530 nM |
| Compound 1D | 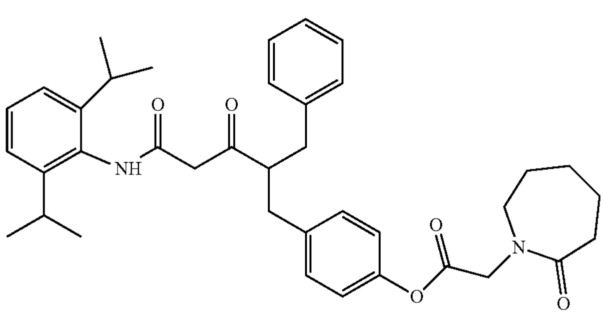 [SMILES: CC(C)c1cccc(C(C)C)c1NC(=O)CC(=O)C(Cc1ccccc1)Cc1ccc(OC(=O)CN2CCCCCC2=O)cc1] | 3.2 nM | 600 nM |

TABLE 1-continued

| Inhibitor | Structure | IC$_{50}$ ACAT1 | IC$_{50}$ ACAT2 |
|---|---|---|---|
| 1[a] | 2-phenylphenyl-NH-CO(CH$_2$)$_6$CH$_3$ | 61 µM | 230 µM |
| 2[a] | 2-phenylphenyl-NH-CO(CH$_2$)$_7$CH$_3$ | 65 µM | 414 µM |
| 13[a] | 1,3-diphenyl-1H-pyrazol-5-yl-NH-CO(CH$_2$)$_6$CH$_3$ | 24 µM | 53 µM |
| 14[a] | 1,3-diphenyl-1H-pyrazol-5-yl-NH-CO(CH$_2$)$_7$CH$_3$ | 23 µM | 75 µM |
| 16[a] | 1,3-diphenyl-1H-pyrazol-5-yl-NH-(CH$_2$)$_8$CH$_3$ | 39 µM | 97 µM |

[a]Gelain (June 2006) 10th ISCPP, Strasbourg, France.

Desirably, ACAT1 inhibitors of the present invention have an IC$_{50}$ value in the range of 1 nM to 100 µM. More desirably, ACAT1 inhibitors of the invention have an IC$_{50}$ value less than 100 µM, 50 µM, 10 µM, or 1 µM. Most desirably, ACAT1 inhibitors of the invention have an IC$_{50}$ value in the nM range (e.g., 1 nM to 999 nM, or more preferably 1 nM to 50 nM) for human ACAT1.

In particular aspects, the ACAT1 inhibitor is F12511, or an analog thereof.

F12511

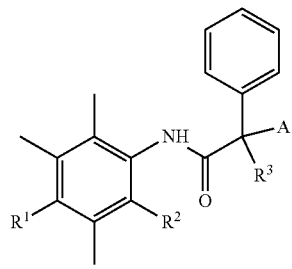

(Eflucimibe)

In certain aspects, F12511 and its analogs have the structure of Formula I:

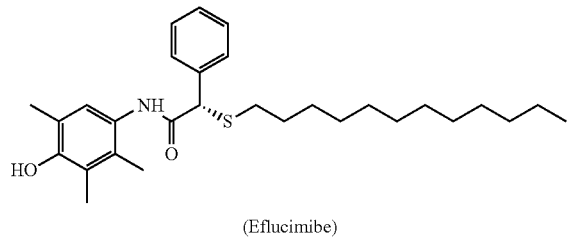

wherein R$^1$ represents a hydroxyl or amino group; R$^2$ represents hydrogen or a methyl radical; R$^3$ represents hydrogen or a fluorine atom; A represents a group

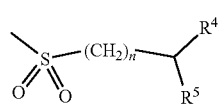
a)

wherein n represents an integer from 5 to 11; R$^4$ and R$^5$, which may be identical or different, represent, independently of one another, hydrogen, or a fluorine atom; or

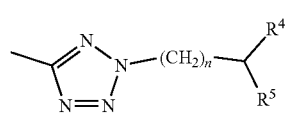
b)

wherein n, R$^4$ and R$^5$ have the same means as above. See US 2006/0135785.

In particular aspects, the ACAT inhibitor is F12511 or an analog having a structure provided in Table 2. Since analog 2 is a slight modification of F12511, and analog 1 and analog 2C are slight modifications of F26, it is expected that these compounds will be comparable to inhibiting ACAT1 as F12511 and F26. In particular, it has been found that the asymmetric carbon in F12511 and in F26 is needed for activity as an ACAT inhibitor and each of analogs 1, 2 and 2c have the asymmetric carbon.

TABLE 2

| Analog[1] | Structure | IC$_{50}$ (µM)[2] |
|---|---|---|
| 1 | 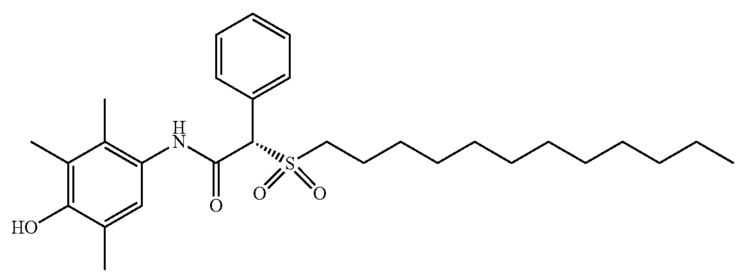 [SMILES: CCCCCCCCCCCCS(=O)(=O)[C@H](C(=O)Nc1cc(C)c(O)c(C)c1C)c1ccccc1] | 135 |
| 2 | 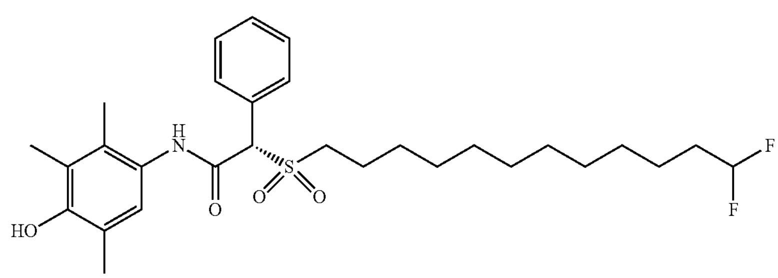 [SMILES: Cc1cc(NC(=O)[C@H](c2ccccc2)S(=O)(=O)CCCCCCCCCCCC(F)F)c(C)c(C)c1O] | — |

TABLE 2-continued

| Analog[1] | Structure | IC$_{50}$ (μM)[2] |
|---|---|---|
| 2c | 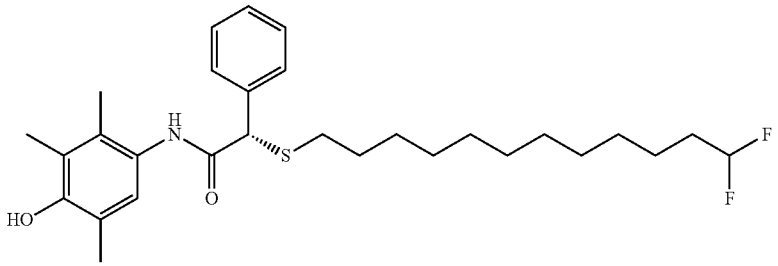 [SMILES: Cc1cc(NC(=O)[C@@H](SCCCCCCCCCCCC(F)F)c2ccccc2)c(C)c(C)c1O] | — |
| 3 (F26) | 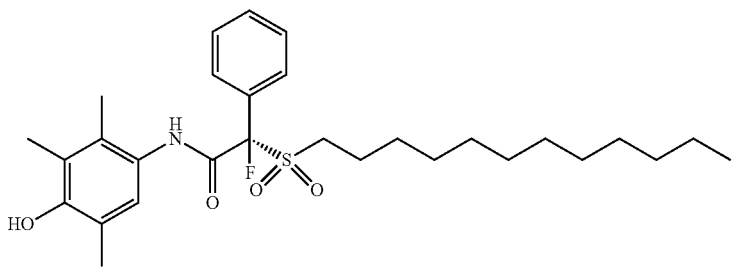 [SMILES: CCCCCCCCCCCCS(=O)(=O)[C@](F)(C(=O)Nc1cc(C)c(O)c(C)c1C)c1ccccc1] | 48 |

[1]Compounds disclosed in U.S. 2006/0135785.
[2]IC$_{50}$ values determined using rat liver microsome as ACAT enzyme source.
Note that the predominant ACAT in rat liver is ACAT2.

In addition to the above-referenced ACAT1 inhibitors, it is contemplated that a drug screening assay can be used for identifying or selecting additional or more selective ACAT1 inhibitors or derivatives or analogs of known ACAT1 inhibitors. See, e.g., Lada, et al. (2004) J. Lipid Res. 45:378-386. Inhibitors of use in the invention can be derivatives of known ACAT inhibitors, which are selective for ACAT1 or can be identified and obtained from libraries of compounds containing pure agents or collections of agent mixtures. In particular, using F12511 and its analogs as lead compounds, additional analogs with chemical modifications can be synthesized to increase bioavailability in the brain, or to increase their biostability in vivo, while maintaining potency in inhibiting both ACAT1 and/or ACAT2.

Known ACAT inhibitors include derivatives of anilidic, ureidic or diphenyl imidazole compounds.

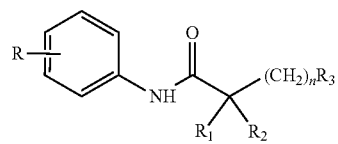

Anilidic Inhibitors

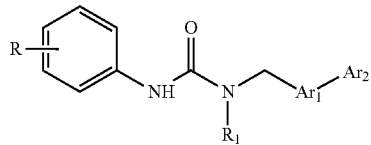

Ureidic Inhibitors

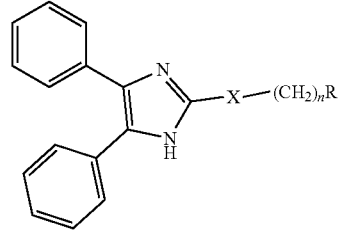

Diphenyl Imidazole Inhibitors

Examples of pure agents for library screens include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernatants. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis, or complex formation. Each resulting subfraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotometers, calorimeters, and fluorimeters, and devices that measure the decay of radioisotopes. It is contemplated that any suitable ACAT enzymatic assay can be used in such screening assays. Moreover, preclinical efficacy of ACAT1 inhibitors can be assessed using conventional animal models of neuroinflammation.

As disclosed herein, there are a number of suitable molecules that selectively inhibit the activity of ACAT1 without modulating the expression of ACAT1. Thus, in some aspects, there are provided compounds that selectively inhibit the expression of ACAT1. Accordingly, an "inhibitor of ACAT1" or "ACAT1 inhibitor" may also include molecules such as small inhibitory RNA (siRNA), antisense molecules, or ribozymes. However, in alternative aspects, the ACAT1 inhibitor is a molecule, which selectively inhibits the expression of ACAT1, without modulating the expression of ACAT2. As is conventional in the art, siRNA or microRNA refer to non-coding RNAs from 19-25 nucleotides in length derived from endogenous genes that act as post-transcriptional regulators of gene expression. They are processed from longer (ca 70-80 nucleotide) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes. By way of illustration, target sequences for siRNA or artificial microRNA molecules against mouse ACAT1 gene include, but are not limited to, those listed in Table 3 as SEQ ID NOs:1-4. SiRNA or artificial microRNAs against human ACAT1 gene (e.g., GENBANK Accession No. NM_000019, incorporated by reference) were also generated and shown to decrease human ACAT1 protein expression by 80% in human cells. Exemplary microRNA sequences targeting human ACAT1 include, but are not limited, those listed in Table 4. In a similar manner, artificial microRNA against the ACAT1 gene in primates (e.g., GENBANK Accession No. XM_508738, incorporated by reference) can be developed, and used to selectively inhibit the expression of primate ACAT1.

Artificial microRNA or siRNA molecules that selectively inhibit the expression of ACAT1 can be administered as naked molecules, delivered via liposomes or exosomes, or via vectors (e.g., a plasmid or viral vector such as an adenoviral, lentiviral, retroviral, adeno-associated viral vector or the like) harboring nucleic acids encoding the microRNA. Desirably, a vector used in accordance with the invention provides all the necessary control sequences to facilitate expression of the microRNA. Such expression control sequences can include but are not limited to promoter sequences, enhancer sequences, etc. Such expression control sequences, vectors and the like are well-known and routinely employed by those skilled in the art.

As demonstrated herein, the addition of between 3 mM and 6 mM phosphatidylcholine to DSPE-PEG$_{2000}$ prior to nanoparticle formation yielded the incorporation of between 6 mM and 12 mM F12511 or K-604. Accordingly, in particular aspects the nanoparticles encapsulate between 5 mM and 20 mM, preferably between 10 mM and 15 mM, most preferably 12 mM ACAT inhibitor. Ideally, the ratio of ACAT inhibitor to phosphatidylcholine is in the range of about 0.3:1 to 2:1, or more preferably 2:1.

While the nanoparticle can be composed solely of a pegylated phospholipid, phosphatidylcholine and an ACAT inhibitor, the nanoparticle may further be modified to include a targeting ligand. By "targeting ligand" is meant a molecule that targets a physically associated molecule or complex to a targeted cell or tissue. As used herein, the term "physically associated" refers to either a covalent or non-covalent interaction between two molecules. A "conjugate" refers to the complex of molecules that are covalently bound to one another. For example, the complex of a lipid covalently bound to a targeting ligand can be referred to as a lipid-targeting ligand conjugate.

Alternatively, the targeting ligand can be non-covalently bound to a lipid. "Non-covalent bonds" or "non-covalent interactions" do not involve the sharing of pairs of electrons, but rather involve more dispersed variations of electromagnetic interactions, and can include hydrogen bonding, ionic interactions, Van der Waals interactions, and hydrophobic bonds.

Targeting ligands can include, but are not limited to, small molecules, peptides, lipids, sugars, oligonucleotides, hormones, vitamins, antigens, antibodies or fragments thereof, specific membrane-receptor ligands, ligands capable of reacting with an anti-ligand, fusogenic peptides, nuclear localization peptides, or a combination of such compounds. Non-limiting examples of targeting ligands include transferrin, OX26, melanotransferrin, insulin, ApoE, leptin, thiamine or vitamin B12, rabies virus glycoprotein (RVG), cell penetrating peptides such as TAT peptide, and monoclonal and polyclonal antibodies directed against cell surface molecules. The targeting ligand can be covalently bound to the lipids of the nanoparticle using techniques known in the art (Ishida et al. (1999) FEBS Lett. 460:129-133; Perouzel et al. (2003) Bioconjug. Chem. 14:884-898).

As indicated, encapsulated inhibitors of ACAT1 find application in methods for reducing or attenuating neuroinflammation, amyloidopathy or tauopathy and/or preventing or treating conditions resulting form or associated with said neuroinflammation or aberrant amyloid or tau. Neuroinflammation is inflammation of the nervous system, including the central nervous system (CNS). Neuroinflammation can be acute, such as an infection or traumatic event, or chronic, such as a neurodegenerative disease (including demyelinating diseases such as Alzheimer's disease (AD), Parkinson's disease (PD), and multiple sclerosis (MS)). In the CNS, glial cells, including microglia and astrocytes, play an important role in innate immunity. Among other cell types in the brain, these cells can produce cytokines and chemokines that act as neuromodulators. The production of pro-inflammatory compounds can cause neurotoxicity and can compromise the integrity of the blood brain barrier (BBB). Accordingly, use of one or more selective inhibitors of ACAT1 can decrease or eliminate expression of pro-inflammatory response genes (e.g., IL-1β, iNOS, MCP1, Cxcl9, Cxcl10 and IL-6) and/or increase or enhance expression of anti-inflammatory response genes (e.g., YM1) thereby providing a benefit to a subject with neuroinflammation.

Tau is a highly soluble protein and is associated with microtubules. It can dimerize, oligomerize, then aggregate in vivo. Oligomerized tau is suggested to be the toxic species that causes tauopathy. Tau oligomerization can occur without hyperphosphorylation and when it is associated with the microtubules. Tau is phosphorylated at different sites. Phosphorylation at the 231st threonine, recognized by the specific antibody Thr231, occurs before aggregation. This phosphorylation diminishes the ability of tau to bind to microtubules. Phosphorylation at Ser202 and Thr205 occurs when tau is aggregated, and has been used as a marker for late-stage tau aggregation. As demonstrated herein, nanoparticle encapsulated ACAT inhibitor F12511 or F26, reduces total unaggregated human tau (htau) as well as aggregated and hyperphosphorylated htau, as determined using antibody ATB, which recognizes phosphorylated Ser202 and Thr205.

Generally, the methods of the invention involve administering to a subject in need of treatment an ACAT1 inhibitor encapsuled in a stealth nanoparticle in an amount that effectively reduces the activity of ACAT1 by at least 60%, 70%, 80%, 90%, 95%, 99% or 100%. Subjects benefiting from treatment with an agent of the invention include subjects exhibiting signs or symptoms of neuroinflammation, amyloidopathy and/or tauopathy or having a condition associated with or resulting from neuroinflammation or aberrant amyloid or tau. Subjects benefiting from treatment with an agent of the invention include those with a neurodegenerative disease (e.g., AD, tauopathy, vascular dementia, PD, Huntington's disease (HD), frontotemporal dementia, amyotrophic lateral sclerosis), neuroinflammatory disorder (e.g., acute disseminated encephalomyelitis, acute optic neuritis, transverse myelitis or neuromyelitis optica), traumatic brain injury or glioma. In the context of this invention, a subject can be any mammal including human, companion animals (e.g., dogs or cats), livestock (e.g., cows, sheep, pigs, or horses), or zoological animals (e.g., monkeys). In particular aspects, the subject is a human.

While certain aspects of this invention embrace in vivo applications, in vitro use of agents of the invention are also contemplated for examining the effects of ACAT1 inhibition on cell expression of Acat1 or activity of ACAT1. In addition to treatment, agents of the invention also find application in monitoring the phenotypic consequences (e.g., expression or activity of cytokines and chemokines, etc.) of neuroinflammation.

For therapeutic use, encapsulated ACAT1 inhibitors can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, PA, 2000. A pharmaceutically acceptable carrier, composition, or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous, or intramuscular injection), topically, orally, intranasally, intravaginally, or rectally according to standard medical practices. Alternatively, the composition can be administered directly to the brain of the subject by a shunt or a catheter. In particular aspects, the pharmaceutical composition is formulated for intravenous or intraperitoneal delivery.

In certain aspects of the present invention, the encapsulated ACAT1 inhibitor is selectively delivered to the brain. For the purposes of the present invention, "selective delivery to the brain" or "selectively delivered to the brain" is intended to mean that the agent is administered directly to the brain of the subject (e.g., by a shunt or catheter; see, e.g., US 2008/0051691), to the perispinal space of the subject without direct intrathecal injection (see, e.g., U.S. Pat. No. 7,214,658), or in a form which facilitates delivery across the blood brain barrier thereby reducing potential side effects associated with ACAT1 inhibition in other organs or tissues. In this regard, formulation of the agent into a nanoparticle in the presence of a stabilizer allows passage of the blood brain barrier without affecting other organs with the agent. See, e.g., U.S. Pat. No. 7,402,573, incorporated herein by reference in its entirety. Furthermore, an exemplary system for selectively delivering microRNAs to the brain is the Adeno-Associated Virus (AAV) vector system. See, e.g., Cearley & Wolfe (2007) J. Neurosc. 27(37):9928-9940.

It has been shown that exosomes (i.e., natural transport nanovesicles in the range of 40-100 nm), which express Lamp2b fused to the neuron-specific rabies viral glycoprotein (RVG) peptide, can deliver siRNA specifically to neurons, microglia, and oligodendrocytes in the brain, thereby resulting in specific gene knockdown (Alvarez-Erviti, et al. (2011) Nature Biotechnol. 29:341-345). Accordingly, in an alternative aspect, the ACAT1 inhibitor is delivered to the brain via an exosome, in particular an exosome modified with a moiety that targets cells of the brain. Exosomes of use in this invention can be prepared by methods such as those described by, e.g., Sun, et al. (2010) Mol. Ther. 18:1606-1614. Likewise, therapeutic agents can be encapsulated within exosomes by methods such as incubating the therapeutic agent with an exosome preparation in saline at room temperature for several minutes, and separating the exosomes from unencapsulated drug and debris, e.g., by sucrose gradient separation. As described in the art, moieties that target cells of the brain include peptides that target cells of the brain (e.g., neurons, microglia and/or oligodendrocytes) as well as other targeting agents such as lipopolysaccharide, which has a high affinity for surface markers on microglia (Chow, et al. (1999) J. Biol. Chem. 274:10689-10692). Targeting peptides include, e.g., the RVG peptide, which may be fused to membrane bound proteins, e.g., Lamp2b (Lysosome-associated membrane protein 2b) to facilitate integration into the exosome. Moreover, when the agent is a nucleic acid (e.g., siRNA or miRNA), the targeting peptide can be fused with a polyarginine peptide (e.g., nine D-arginines) so that the nucleic acid is electrostatically bound to the targeting moiety. In addition to using exosomes for delivery of the compositions, one of skill would understand that untargeted or brain-targeted liposome has been used successfully to facilitate delivery of the siRNA or small molecule inhibitors to brain tissue (Pardridge (2007) Adv. Drug Deliv. Rev. 59:141-152; Pulford, et al. (2010) PLoS ONE 5:e11085). As a result, aspects of the methods of the present invention include using of liposomes that are either targeted or untargeted.

In another alternative aspect, the ACAT1 inhibitor is delivered intranasally via an exosome. Curcumin or Stat3 inhibitor, JSI-124 (cucurbitacin I), delivered via exosomes to the brain via the nasal route has been shown to accumulate in microglia and inhibit lipopolysaccharide (LPS)-induced microglial cell activation, delay experimental autoimmune encephalomyelitis (EAE) disease, and inhibit tumor growth in vivo (Zhuang, et al. (2011) Mol. Ther. 19:1769-1779). It is posited that transport occurs along the olfactory pathway and likely involves extracellular bulk flow along perineuronal and/or perivascular channels, which allows for delivering drugs directly to the brain parenchyma. Delivery along the extraneuronal pathway is likely not receptor-mediated and requires only minutes for a drug to reach the brain; whereas, delivery via an intraneuronal pathway along the primary olfactory sensory neurons involves axonal transport and requires several days for the drug to reach different areas of the brain. Therefore, in certain aspects, the ACAT1 inhibitor of the invention is delivered to the brain, in particular microglia, by encapsulating within exosomes and intranasal administration.

For encapsulation in a nanoparticle, F12511 is prepared at 10 mM. Once injected into the blood, its concentration is expected to be diluted to approximately 1 mM. Based on HPLC quantitation analyses of F12511 in the blood, F12511 undergoes degradation more rapidly than that of the nanoparticle. However, its concentration in the blood is high enough that a substantial portion of F12511 (approximately 0.1% to 0.2%) enters the brain to provide significant inhibition of ACAT activity in the brain. Indeed, as demonstrated herein, a DSPE-PEG$_{2000}$- and phosphatidylcholine-based nanoparticle incorporated a high concentration of ACAT1 inhibitor, provided a high level of ACAT1 inhibitor in the blood, entered the CNS, and inhibited ACAT1 in the brain significantly for a prolonged period of time (longer than 8 hours). Thus, in certain aspects, the ACAT1 inhibitor is encapsulated in a nanoparticle that maintains a concentration of the inhibitor in the blood of the subject at above 20 µM for at least 4 hours or 8 hours, thereby providing therapeutic benefit.

In a further alternative aspect, the ACAT1 inhibitor is encapsulated in human serum albumin (HSA) nanoparticles to enhance solubility and bioavailability of the inhibitor. Such nanoparticles can be fabricated via unfolding of HSA in appropriate solution to expose more hydrophobic domains and consequent self-assembling into nanoparticles with the ACAT inhibitor. See Zhou, et al. (2016) Anticancer Res. 36(4):1649-56; Ding, et al. (2014) AAPS PharmSciTech. 15(1):213-22.

To enhance treatment of one or more the disorders, disorders or conditions described herein, the ACAT1 inhibitor may be administered in combination with a second therapeutic agent that complements the action of the ACAT1 inhibitor. Ideally, the second therapeutic agent may target a cause of the underlying disease or condition, e.g., misfolded/aggregated protein/peptide such as amyloid 3 in AD, tau in AD, α-synuclein in PD, and frontotemporal dementia, and huntington in HD. Examples of second therapeutic agents of use in combination with the ACAT1 inhibitor include, but are not limited to, β-secretase inhibitors/modulators (e.g., AZD3293, CTS-21166, E2609, HPP854, LY2886721, MK-8931, PF-05297909, RG7129 or TK-070), γ-secretase modulators (e.g., LY-411575, LY-450139, begacestat, ELN-475516, BMS-708163, MRK-003, CHF5074 or R04929097), proteasome inhibitors (e.g., Bortezomib), small molecule activators of the unfolded protein response (e.g., Celastrol), Hsp90 inhibitors (e.g., Geldanamycin), small molecule Hsc70 inhibitors (e.g., YM-01), deubiquitination enzyme inhibitors (e.g., siRNA targeting Usp14), epigallocatechin-3-gallate, variants of Hsp104 disaggregase, glutathione ethyl ester, and antibodies (e.g., anti-oligomeric amyloid β antibody, anti-tau antibody, anti-α-synuclein antibody or anti-huntington antibody). When included, the second therapeutic agent can be co-administered as a conventional pharmaceutical composition along with the nanoparticle encapsulated ACAT inhibitor, administered in the same nanoparticle as the ACAT inhibitor, or co-administered in a separate nanoparticle along with the nanoparticle encapsulated ACAT inhibitor. As with the ACAT inhibitor, administration of the second therapeutic agent via a nanoparticle will allow for the second therapeutic agent to enter the brain interior and provide therapeutic benefit.

The selected dosage level of an ACAT1 inhibitor and optional second therapeutic agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required based upon the administration of similar compounds or experimental determination. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

A further aspect of this invention provides a method for reducing or attenuating amyloidopathy or tauopathy by administering to a subject in need thereof a nanoparticle having a core and an outer lipid envelope, wherein the outer lipid envelope is composed of DSPE-PEG and PC. While the core of the nanoparticle may include a solvent (e.g., water, saline and the like), such nanoparticles may be devoid of a therapeutic agent as it has been demonstrated herein that empty nanoparticles exhibit a therapeutic benefit. Alternatively, the nanoparticles may encapsulate an ACAT inhibitor or other therapeutic agent (see the second therapeutic agents disclosed herein). Moreover, the DSPE-PEG/PC-based nanoparticle may be modified to include one or more additional lipids, e.g., sphingomyelin, cholesterol, ceramide, cardiolipin, as well as other minor lipid species, to increase potency in reducing or attenuating amyloidopathy and/or tauopathy.

Ideally, the DSPE-PEG to PC ratio is in the range of 30:3 to 30:12, or more preferably 30:6. Moreover, in certain aspects, the concentration of PC is greater than or equal to 6 mM. Advantageously, nanoparticle composed of 30 mM DSPE-PEG and 6 mM PC can provide 3 mM DSPE-PEG and 0.6 mM PC in the blood of a patient immediately upon delivery of the nanoparticle and provide therapeutic benefit by reducing or attenuating amyloid burden and aggregated and hyperphosphorylated htau but not total unaggregated human tau.

The invention is described in greater detail by the following non-limiting examples.

Example 1: Material and Methods

Lipids, ACAT Inhibitors, and Solvents: DSPE-PEG$_{2000}$ was from Laysan Bio, Inc (mPEG-DSPE, MW 2,000). L-α-Phosphatidylcholine was from Sigma-Aldrich. F12511 and K-604 were custom synthesized by WuXi AppTec in China. Based on HPLC/MS and NMR profiles, purity of F12511 was 98% and in stereospecificity; purity of K-604 was 98% in chemical purity. Organic solvents were from Fisher Scientific.

Mice. Mice were fed ad libitum with standard chow diet, maintained in a pathogen-free environment in single-ventilated cages and kept on a 12-hour light/dark schedule.

Generation of Acat1$^{-/-}$ Alz (A1$^{-}$/Alz) and Acat2$^{-/-}$ Alz (A2$^{-}$/Alz) Mice. Acat1$^{-/-}$ and Acat2$^{-/-}$ mice (Meiner, et al. (1996) Proc. Natl. Acad. Sci. USA 93:14041-14; Buhman, et al. (2000) Nat. Med. 6:1341-1347) in C57BL/6 background are known in the art. The 3XTg-Alz mice (Alzheimer's disease mice) in hybrid 129/C57BL/6 background contain two mutant human transgenes, hAPP harboring Swedish mutation (hAPPswe), and mutant htau (htau$_{P301L}$) under a neuron-specific promoter, and contain the knock-in mutant presenilin 1 (PS1$_{M146V}$) (Oddo, et al. (2003) Neuron 39:409-421).

Cell Culture. Cell lines were kept in a 37° C. incubator with 5% CO$_2$. Human neuron-like SH-SY5Y cells were maintained in 1:1 EMEM (Corning, Manassas, VA):Ham's F-12 (Sigma, St. Louis, MO) medium supplemented with MEM non-essential amino acids (Gibco, Grand Island, NY) and 10% calf serum (R&D Systems, Flowery Branch, GA). Human microglia-like HMC3 cells (ATCC) were maintained in MEM (Corning, Manassas, VA) medium with 10% calf serum. Mouse neuron-like N2a cells were maintained in 1:1 DMEM (Corning, Manassas, VA):MEM (Corning, Manassas, VA) medium with 10% calf serum. Mouse microglia-like N9 cells were maintained in RPMI (Corning, Manassas, VA) medium with 10% calf serum.

Primary cortical neurons were dissected from E14.5-16.5 embryos from C57/BL6 mice and plated at 50,000 cells per well in precoated poly-D-lysine (Sigma-Aldrich, St. Louis, MO) and laminin-coated (Sigma-Aldrich, St. Louis, MO) 96-well tissue culture dishes. Cells were incubated in enriched neurobasal (NB) medium (Thermo Fisher Scientific, Waltham, MA) (500 mL NB media, 200 mM L-glutamine, B-27 with vitamin A, 1 mL penicillin-streptomycin (1%), and 340 mg glucose). Neurons were allowed to grow processes for 4-6 days prior to treatment.

Isolation of Microglia from Adult Mouse Brain. Microglia cells were isolated from adult mouse brains using CD11b MicroBeads (Miltenyi Biotec, San Diego, CA) as described previously (Nikodemova & Watters (2012) J. Neuroinflamm. 9:147). The CX3CR1/GFP$^{+/+}$ mice were used to examine the purity of microglia; GFP expression within the central nervous system of this mouse line is almost exclusively in microglia (Jung et al. (2000) Mol. Cell. Biol. 10:4106-14).

F12511 LC-MS/MS Protocol. F12511 and internal standard CP113,818 were quantified in mouse tissues via LC-MS/MS. Both compounds were dissolved in DMSO at 10 mg/mL and stored at −40° C. Subsequent working dilutions were made in acetonitrile (ACN) fresh daily. Calibrators and quality controls were made in the appropriate matrix: C57BL6 plasma (anticoagulant: K3-EDTA, Innovative Research), C57BL6 whole blood (anticoagulant: K3-EDTA, Innovative Research), C57BL6 brain homogenate (study provided), or C57BL6 liver homogenate (study provided). Tissues were homogenized at 0.1 g/mL in diH$_2$O using stainless steel beads and a Next Advance Bullet Blender. All samples (50 μL) were protein precipitated with 150 μL 10 ng/mL CP113,818 in ACN via vortex 1 minute and centrifugation 5 minutes at 15,000 rpm. 150 μL of supernatant was transferred to amber autosampler vials and 10 μL was injected on the LC-MS/MS system.

HPLC separation was achieved with isocratic conditions of 5% diH$_2$O, 95% methanol, and 0.1% formic acid over 2.5 minutes at a flow rate of 1.5 mL/min on a Phenomenex Luna C18 100×4.6 mm, 3 micron column fitted with a 10×4 mm C18 guard at 40° C. A TSQ Vantage mass spectrometer was operated in positive ion mode with a collision pressure of 1.3 mTorr to measure F12511 (470.242→268.120 m/z) and CP113,818 (471.177→201.040 m/z) with collision energies of 16 and 21, and SLens values of 139 and 187, respectively. The heated ESI source was operated with a spray voltage of 4500 V, vaporizer temperature 500° C., capillary temperature 250° C., sheath and auxiliary gases at 30 and 15 arbitrary units, respectively. The quantitative range was 0.3-1000 ng/mL for liver, brain, and whole blood, and 0.5-1000 ng/mL for plasma with the following inter- and intraday confidence values (CV) and accuracies (Ac) of across three quality control levels: plasma intraday CV 3-14%, Ac 86-109%; plasma interday CV 13-15%, Ac 95-100%; liver intraday CV 2-10%, Ac 93-114%; liver interday CV 5-8%, Ac 94-111%; whole blood intraday CV 3-10%, Ac 85-115%; whole blood interday CV 12-14%, Ac 96-115%; brain intraday CV 2-11%, Ac 94-115%; brain interday CV 9-14%, Ac 96-108%.

Nanoparticle Formation. Nanoparticles were prepared according to a general method (Gülçür, et al. (2013) Drug Deliv. Transl. Res. 3(6):562-574; Jhaveri & Torchilin (2014) Front. Pharmacol. 5:77) with modifications. Using a clean glass tube (9 mL capacity), 60 mg of DSPE-PEG$_{2000}$ was dissolved in 500 μL of ethanol (EtOH) for a working concentration of 60 mM. Phosphatidylcholine (PC) (dissolved in chloroform) was added at working concentrations ranging from 0 to 12 mM to the DSPE-PEG$_{2000}$ solution while vortexing. F12511 was dissolved in 500 μL of ethanol at working concentrations of 12-24 mM then added to the DSPE-PEG$_{2000}$/PC mixture while vortexing. The final solution contained concentrations of 30 mM DSPE-PEG$_{2000}$, 0-6 mM PC, and 6-12 mM F12511. The final solution was then lyophilized under refrigeration overnight to remove organic solvent. The sample was re-suspended in 1 mL of phosphate-buffered saline (1X) (PBS) and vortexed until the sample was in suspension. This step took approximately 1 hour as the sample needed to rest between repeated vortexing to prevent excessive foaming. Once in fine suspension, the sample was purged with nitrogen, capped, wrapped with parafilm, and bath sonicated (Branson 2510 model) at 4° C. for 2-4 rounds at 20 minutes per round. DSPE-PEG$_{2000}$/PC nanoparticles without F12511 were clear while F12511/DSPE-PEG$_{2000}$/PC nanoparticles (Nanoparticle F) were slightly turbid and contained some visible precipitate. After sonication, nanoparticles were transferred to sterile Eppendorf tubes and centrifuged at 12,000 rpm for 5 minutes to remove unincorporated materials. The supernatant as well as the pellet were collected for chemical analysis. In some experiments, the nanoparticles were loaded onto a 5 mL SEPHAROSE® (crosslinked agarose) CL-4B column. SEPHAROSE® CL-4B contains beads with particle size at 45-65 µm. The column (approximately 28 mm circumference) was first equilibrated with PBS at room temperature, then loaded with the 1 mL of sample, eluted with PBS and fractions of 500 µL to 1 mL were collected. This method was used to assure that F12511 or K-604 encapsulated in nanoparticles did not appear in the exclusion volume of the SEPHAROSE® CL-4B column.

Nanoparticle Analysis. To confirm the concentration of F12511 (or K-604) and DSPE-PEG$_{2000}$/PC in the nanoparticles, 10 µL of each sample component were loaded onto a thin layer chromatography (TLC) plate (Analtech Silica gel HL). The solvent systems used were hexanes:ethyl ether: acetic acid (60:40:1) (Bryleva, et al. (2010) Proc. Natl. Acad. Sci. USA 107(7):3081-3086) to detect F12511 and chloroform:methyl acetate:isopropanol:methanol:water (28:25:25: 12:10) to detect K-604. The retention factor (Rf) was approximately 0.35 for F12511 and approximately 0.5 for K-604. The content of F12511 or K-604 was determined by extrapolation from a standard curve of a concentration gradient of the respective compound produced in the same TLC plate. The plate was stained with iodine and quantified using ImageJ. The TLC/iodine stain method detected F12511 or K-604, and DSPE-PEG$_{2000}$/PC separately, thus allowing for encapsulation efficiency determination.

Dynamic Light Scattering (DLS) Measurements. Nanoparticle sizes were measured with Malvern Panalytical Zetasizer Nano-ZS, using 10 mm path length disposable cuvettes. Samples were kept in 4° C. in tubes wrapped with parafilm and left in the dark whenever possible. Prior to analysis, samples were centrifuged for 5 minutes at 12,000 rpm. Most samples required 2-fold dilution to get an accurate reading. Samples were measured in triplicate.

Intact Cell Cholesteryl Esterification by $^3$H-Oleate Pulse. Using an established procedure (Chang, et al. (1986) Biochemistry 25(7):1693-1699), monolayers of cells were treated for 2 hours with various concentrations of either control (ethanol or PBS), DSPE-PEG$_{2000}$/PC nanoparticles, F12511 (dissolved in ethanol), or F12511/DSPE-PEG$_{2000}$/PC (Nanoparticle F) nanoparticles. Following treatment, cells were pulsed at 37° C. for 1-3 hours with $^3$H-oleate/fatty acid free BSA, then washed with cold PBS, lysed by adding cold 0.2 M NaOH at appropriate volume, and placed on orbital shaker for 40 minutes. The solubilized cell slurries were collected into glass tubes, neutralized with 3M HCl, and lipids were extracted with CHCl$_3$:MeOH (2:1) and water. Samples were vortexed and centrifuged at 500 rpm for 10 minutes. The top-phase was removed, and the bottom phase was blown dry with N$_2$ using N-evap apparatus (Organomation Associates, Inc.). Dried samples were vortexed with ethyl acetate and spotted on TLC plate. The solvent system used was petroleum ether:ethyl ether:acetic acid (90:10:1). The cholesteryl ester band was scraped from the TLC plate and measured with a scintillation counter for radioactivity.

In vitro Mixed Liposomal ACAT Activity Assay. Using an established procedure (Chang, et al. (1998) J. Biol. Chem. 273(52):35132-35141; Neumann, et al. (2019) Arch. Biochem. Biophys. 671:103-110). Monolayers of cells were treated for 4 hours with either control (dimethyl sulfoxide (DMSO)), or with 0.5 µM F12511 in DMSO. Cells were then washed with drug-free medium kept at 37° C. for various amounts of time. At the indicated times, cells were washed with cold PBS, then lysed in a 2.5% 3-((3-Cholamidopropyl) dimethylammonio)-1-propanesulfonate (CHAPS), 1M KCl in 50 mM Tris at pH 7.8 buffer. Lysed cells were collected and aliquoted into pre-chilled tubes containing the liposomal mixture of taurocholate, phosphatidylcholine, and cholesterol. Tubes were vortexed and kept on ice for 5 minutes. Samples were then incubated in a 37° C. shaking water bath with $^3$H-oleoyl CoA added for 10 minutes. The assay was stopped by adding CHCl$_3$:MeOH (2:1). Lipids were extracted and analyzed by the same TLC method described herein.

Lactate Dehydrogenase (LDH) Toxicity Assay. Primary cortical neurons were harvested and maintained as described above. Neurons were treated with either F12511 alone (dissolved in EtOH), F12511/DSPE-PEG$_{2000}$/PC nanoparticles (Nanoparticle F), or DSPE-PEG$_{2000}$/PC nanoparticles at 2-100 µM concentrations for 24-, 48-, or 72-hours. After treatment, the conditioned media from the cells were collected, spun at 12,000 rpm for 30 minutes to remove cellular debris, supernatant transferred to new tube, and frozen at −80° C. until time of assay. Using Cytotoxicity Detection Kit (LDH) (Roche), media and reaction mixture were mixed, incubated for 30 minutes at room temperature protected from light, and the absorbance was measured at 490 nm.

Example 2: MicroRNA-Mediated Inhibition of ACAT1 Expression

Artificial microRNA molecules were designed to target the 5' end of the coding sequence of mouse ACAT1 sequences listed in Table 3.

TABLE 3

| microRNA | ACAT1 Target Sequence | SEQ ID NO: |
|---|---|---|
| #52 | GGAGCTGAAGCCACTATTTAT | 1 |
| #53 | CTGTTTGAAGTGGACCACATCA | 2 |
| #54 | CCCGGTTCATTCTGATACTGGA | 3 |
| #55 | AACTACCCAAGGACTCCTACTGTA | 4 |

For example, the pre-microRNAs (including sense, antisense and loop regions) of microRNAs #54 and #55 were 5'-TGC TGT CCA GTA TCA GAA TGA ACC GGG TTT TGG CCA CTG ACT GAC CCG GTT CAC TGA TAC TGG A-3' (SEQ ID NO:5) and 5'-TGC TGT ACA GTA GGA GTC CTT GGG TAG TTT TGG CCA CTG ACT GAC TAC CCA AGC TCC TAC TGT A-3' (SEQ ID NO:6), respectively.

NIH-3T3 mouse fibroblasts were transiently transfected with one of several rAAV vectors encoding EmGFP and microRNA (miR) #52, #53, #54 or #55. Forty-eight hours post-transfection, GFP-positive cells were harvested by FACS. GFP-positive cells were washed then lysed in 10% SDS and syringe homogenized. Twenty microgram of protein per sample was subjected to SDS-PAGE. After western blot analysis, bands were quantified with ImageJ. ACAT1 intensity was normalized to GAPDH as a loading control and expressed as relative intensity. The results of this analysis are presented in Table 4.

TABLE 4

| Treatment | Relative Intensity |
|---|---|
| Mock Transfected | 1.00 |
| miR Negative Control | 1.02 |
| miR #52 | 0.77 |
| miR #53 | 0.56 |
| miR #54 | 0.54 |
| miR #55 | 0.39 |

This analysis indicated that microRNA molecules directed to mouse ACAT1 sequences could effectively decrease mouse ACAT1 gene expression by more than 50% compared to untreated controls.

Similarly, upon treatment of human HeLa cells or MCF-7 cells with either of the microRNAs listed in Table 5 (10 nM concentration for two days) decreased human ACAT1 protein expression by 80%.

TABLE 5

| MicroRNA Sequence (5'->3') | SEQ ID NO: |
|---|---|
| CAUGAUCUUCCAGAUUGGAGUUCUA | 7 |
| UAGAACUCCAAUCUGGAAGAUCAUG | 8 |

Example 3: Effect of Recombinant Adeno-Associated Virus Expressing Acat1 siRNA

Four different siRNA molecules (#52-#55; Table 3) targeting the mouse Acat1 gene were inserted into an endogenous mouse microRNA (miR) scaffold using Invitrogen's RNAi design tool. The artificial miRs were ligated into the mammalian expression vector pcDNA6.2-GW/EmGFP-miR. These Acat1miR constructs were tested along with a negative control (NC) miR (5'-TACTGCGCGTGGA-GACG-3'; SEQ ID NO:9), which does not match the sequence of any known vertebrate gene, in NIH-3T3 mouse fibroblasts. The miRs were delivered to the cells using a standard cDNA transfection protocol. The results showed that Acat1 miRs #54 and #55 were effective in causing 50-60% reduction in the ACAT1 protein content in treated mouse 3T3 fibroblasts.

MicroRNAs #54 and #55, and the NC miR molecule were also subcloned into a rAAV backbone vector (AAV-6P-SEWB) that contained the neuron-specific hSyn promoter (Sibley et al. 2012. Neel. Acids Res. 40:9863-9875). This vector contained a strong nonspecific promoter that expressed Acat1 miRs in any cell type where the viral genome was expressed. For identification purposes, it also co-expressed GFP with the miRs. These three constructs were used to produce three recombinant AAV viruses. To test the efficacy and specificity of these viruses, cultured primary hippocampal neurons were treated with the NC AAV, or with AAV that expressed miR containing siRNA Acat1 #55. Two weeks after viral infection, the effects of AAVs on cholesteryl ester biosynthesis were tested in neurons. The results showed that the AAV harboring siRNA Acat1 #55 reduced cholesteryl ester biosynthesis by more than 50% (P<0.01), when compared with values in NC virus treated cells.

Example 4: Quantification of F12511

To quantify the F12511 content in nanoparticles, a thin layer chromatography (TLC) method followed by iodine staining and ImageJ analysis was developed. The TLC system used clearly separated F12511 or K-604 from DSPE-PEG$_{2000}$/PC. To determine the amount of F12511 in the nanoparticles, different concentrations of F12511 (5-60 µg) were spotted onto a TLC plate along with the actual sample. After TLC and iodine stain, a trendline, equation (y=3471.1x+24025), and R-squared value ($R^2$=0.8943) was calculated to produce a standard curve. Using the extrapolated equation, the concentration of F12511 in the nanoparticles was determined using ImageJ analysis.

Example 5: Phosphatidylcholine Improves Encapsulation of F12511 in DSPE-PEG$_{2000}$ Nanoparticles DSPE-PEG$_{2000}$ nanoparticles were prepared to encapsulate F12511 using a lyophilization/resolubilization method. The results showed that this method was effective at encapsulating F12511, but at a low encapsulation efficiency of approximately 6 mol % of DSPE-PEG$_{2000}$. To improve drug solubilization, the inclusion of phosphatidylcholine (PC) in nanoparticles has been suggested (Ashok, et al. (2004) J. Pharmaceut. Sci. 93(10):2476-2487). Accordingly, various amounts of PC (10% or 20%) were added to the DSPE-PEG$_{2000}$ ethanol mixture prior to nanoparticle formation and analysis. As shown by iodine-stained TLC, there was an increase in detectable F12511 with DSPE-PEG$_{2000}$ and 10% PC in the supernatant and the corresponding elution fractions from the size exclusion column. While the addition of PC at 10 mol % of DSPE-PEG$_{2000}$ was able to incorporate about 20 mol % F12511, doubling PC and F12511 concentrations led to a notably higher encapsulation. With 20 mol % (6 mM) PC, the nanoparticles were able to encapsulate approximately 40 mol % (12 mM) F12511; there was a large amount of F12511 detected in the supernatant, as well as in the corresponding eluted fractions from the column, that co-eluted with DSPE-PEG$_{2000}$/PC. Based on several preparations of the nanoparticles made, after fractionation by centrifugation, the result of TLC analysis showed that there was approximately 9 mM of F12511 encapsulated, rather than the full 12 mM present in the unfractionated samples. This nanoparticle system was also effective at encapsulating large concentrations of K-604. Using the same nanoparticle preparation for K-604 (40 mol % K-604 (12 mM), 20 mol % PC (6 mM), and DSPE-PEG$_{2000}$ (30 mM)), a large amount of K-604 was detected in the supernatant. The result of the size exclusion column chromatography also showed that most of the K-604 signal co-eluted with DSPE-PEG$_{2000}$/PC signal and these signals appeared in the column-included fractions. These results showed that this nanoparticle system can be utilized to encapsulate high concentrations of hydrophobic compounds.

The size of the nanoparticles was next characterized quantitatively using dynamic light scattering (DLS) measurements via a Malvern Zeta Sizer. In addition, the same batch of nanoparticles (with or without F12511) were measured monthly to determine stability of the nanoparticles. The results indicated that when the nanoparticles were kept at 4° C. and in the dark, their sizes were essentially unaltered for up to 6 months. Since the nanoparticles were PEGylated, this feature increased the stability of the nanoparticles (Gref, et al. (2000) Colloids Surf. B: Biointerfaces 18(3-4):301-313; Miteva, et al. (2015) Biomaterials 38:97-107; Suk, et al. (2016) Adv. Drug Deliv. Rev. 99:28-51). Interestingly, based on testing different batches of nanoparticles, the results showed that the nanoparticles containing F12511 had one main peak ranging from 170 nm to 250 nm, indicative of unilamellar liposomes, while the "empty" nanoparticles containing only DSPE-PEG$_{2000}$/PC had two peaks at approximately 15-20 nm and 140-160 nm. This was likely due to the DSPE-PEG$_{2000}$ and PC forming separate, smaller micelles (15-20 nm) as well as the unilamellar liposomes with sizes ranging from 140-160 nm. The Zeta Potential for the nanoparticles remained in the low neutral range likely due to the presence of high salt in the PBS used to resolubilize the nanoparticles after lyophilization.

Example 6: F12511 Encapsulated in DSPE-PEG$_{2000}$/PC Nanoparticles Significantly Inhibits ACAT Activity in Mouse and Human Neuronal and Microglial Cell Lines To test the efficacy of the nanoparticles at inhibiting ACAT activity, mouse and human neuronal and microglial cell lines were used. Intact cells were treated with either control (EtOH), DSPE-PEG$_{2000}$/PC nanoparticles, F12511 alone (dissolved in EtOH), or F12511 DSPE-PEG$_{2000}$/PC nanoparticles (Nanoparticle F). The results showed that across all cell lines, both F12511 alone and nanoparticle F12511 tested at 0.04 µM and 0.4 µM significantly inhibited ACAT in a dose dependent manner. These results indicated that nanoparticle F12511 was almost as efficient as F12511 alone in inhibiting ACAT in intact cells, even with a short treatment time of 2 hours. Notably, F12511 alone or nanoparticle F12511 was more effective in inhibiting ACAT in human cell lines (SH-SY5Y and HMC3 cells) than in mouse cell lines (N2A and N9 cells).

F12511 inhibits ACAT1 at high affinity with an IC$_{50}$ value and inhibitory constant (Ki) of 39 nM (Chang, et al. (2000) J. Biol. Chem. 275(36):28083-92). In general, enzyme inhibitors with a low Ki interact with the target enzyme with low dissociation rate. It was posited that once F12511 binds to ACAT1, it may dissociate from the enzyme slowly. This was analyzed at the cellular level by incubating F12511 alone or nanoparticle F12511 in neuronal and microglial cell types. After 2 hours of treatment, media containing F12511 was removed, cells were washed twice with drug-free media, and placed in drug-free media for either 0-, 2-, 4-, or 8-hours. Afterward, the ACAT activity in these cells was measured by performing $^3$H-oleate pulse. The results showed that in F12511 treated cells, ACAT activity remained severely inhibited in all cell types examined, even after 8 hours of drug removal from the media. For nanoparticle F12511 treated cells, ACAT activity also remained severely inhibited for 4-6 hours. At 8 hours, significant inhibition occurred in SH-SY5Y, N2A and N9 cells but not in HMC3 cells. Together, these results indicated that in intact cells, once bound to ACAT1, F12511 slowly dissociates from the enzyme. The validity of these results was analyzed using a different method to monitor ACAT enzyme activity. N9 cells were treated with DMSO as control or with F12511 alone for 4 hours, washed with drug-free media, and incubated in drug-free media for various amounts of time, up to 4 hours. Here, the ACAT activity was monitored using the ACAT enzyme assay in vitro. The in vitro assay monitors the interaction between ACAT and F12511 in the milieu where detergent taurocholate, phospholipid, and cholesterol are present in abundance (Chang, et al. (1998) J. Biol. Chem. 273(52):35132-35141). The results of this analysis showed that, even under this condition, the ACAT enzyme activity stayed inhibited by F12511 for up to 4 hours after F12511 removal from the media. Together, the results of these analyses indicated that once F12511 binds to ACAT, it does not readily dissociate from the enzyme for several hours and the binding between ACAT1 and F12511 is not readily affected by the presence of cholesterol, phospholipids, or detergent.

Example 7: Neuronal Cell Toxicity is Undetectable After Treatment with F12511 Alone or with Nanoparticle F F12511 has been tested in clinical trials for atherosclerosis and passed clinical safety tests; however, its potential toxicity in neurons has not been reported. Accordingly, the potential toxicity of F12511 and Nanoparticle F12511 was tested in primary mouse neuronal cells. Using F12511 concentrations ranging from 2 µM to 100 µM, cells were treated for 24-, 48- or 72-hours and cellular toxicity was assessed by monitoring the leakage of lactate dehydrogenase (LDH). The results showed that for the three different agents tested (F12511 alone, nanoparticle F12511, and DSPE-PEG$_{2000}$/PC vehicle), there was minimal, if any, toxicity after 24 hours of treatment. At 48 hours, there was a slight increase in toxicity for F12511 at very high concentrations (near 100 µM). At 72 hours, more toxicity was detected at this high concentration. Importantly, at 72 hours, only very minimal toxicity occurred after treatment of F12511 alone or with nanoparticle F12511 at concentrations of 10 µM, which was more than two orders of magnitude higher than the Ki for F12511 to inhibit ACAT1/SOAT1 (39 nM). Notably, the treatment time scale for the in vitro cell line analyses was only 2-4 hours, while the time scale in the LDH assays was significantly longer. This indicates that toxicity was not observed within the treatment paradigm used to measure ACAT inhibition and that longer incubations could be performed with minimal toxicity.

Example 8: Delivery of F12511 in Mice Via Nanoparticles

Studies have shown orally administered F12511 has a very short half-life in the blood of mice (1-2 hours) (U.S. Pat. No. 6,864,246). Accordingly, to increase its half-life, F12511 was encapsulated in a non-toxic DSPE-PEG$_{2000}$-based nanoparticle at 6-8 mol % for F12511. For comparison, K-604 was also encapsulated at 40 mol %. The sizes of the F12511, and K-604 nanoparticles were approximately 220 nm (results from a Zeta sizer measurement). Using fresh cell homogenates prepared from intact cells treated with F12511 and K-604 nanoparticles, it was found that the ACAT enzyme activity was effectively inhibited by F12511 (or K-604) in intact cells. This finding is attributed to the high-affinity binding between ACAT1 and F12511 (or K-604).

Figure 1B:
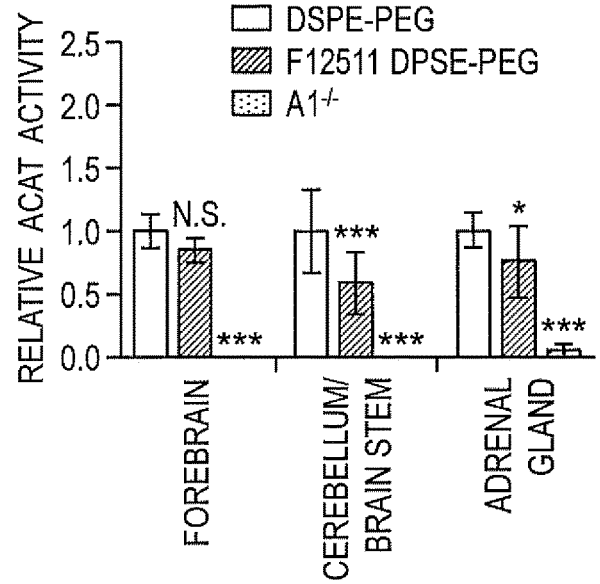
Figure 1C:
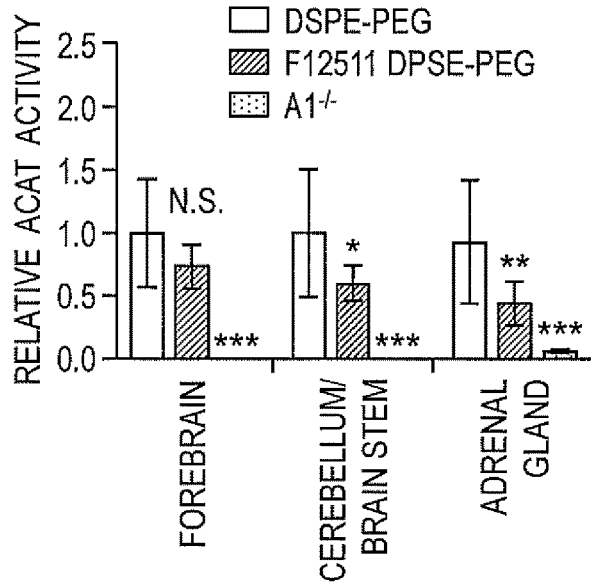
Figure 1D:
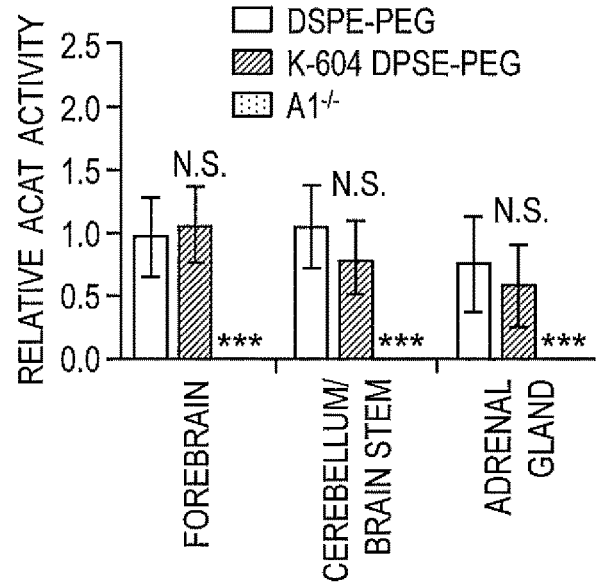

F12511 nanoparticles (at 5 mol % F12511) were subsequently delivered to wild-type mice by a single IV injection, to determine if F12511 could be protected from rapid hepatic clearance. At 1 (FIG. 1A), 4 (FIG. 1B) and 8 (FIG. 1C) hours after injection, various tissues were isolated, tissue homogenates were prepared, and ACAT enzyme activity in vitro was measured. The results showed that one hour after IV injection, F12511 significantly inhibited ACAT activity in the adrenals by more than 50%, and said inhibition was maintained for at least 8 hours. In the cerebellum and brain stem region, F12511 partially inhibited ACAT activity (by nearly 50%) after 4 and 8 hours, but not at the one-hour time period. In the case of K-604-based nanoparticles, K-604 tended to inhibit ACAT activity in the adrenals by the fourth hour (FIG. 1D), but the result did not reach statistical significance. These results showed that F12511 was a more potent ACAT1 inhibitor than K-604 when administered in a nanoparticle via IV injection, F12511 was permeable to the brain, and F12511 inhibitory effect could be sustained for at least eight hours. Accordingly, DSPE-PEG$_{2000}$-based nanoparticles provided significant protection to F12511 from hepatic degradation thereby allowing F12511 to stay in the blood and enter the brain.

Figure 2:
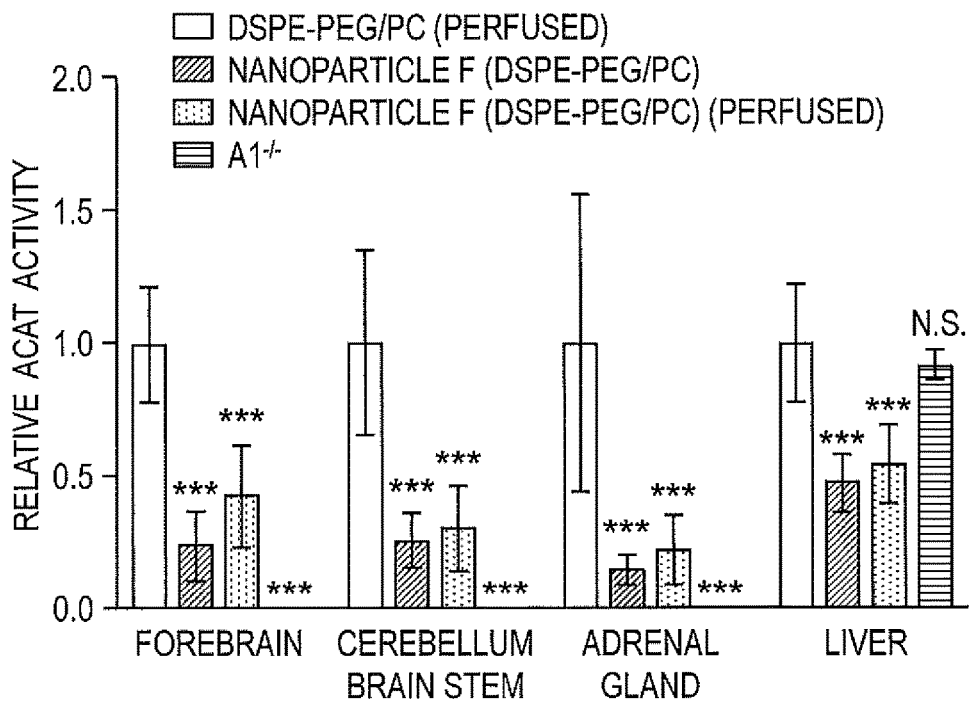
FIG. 2 shows that nanoparticle F12511 (nanoparticle F) reduces ACAT activity more efficiently in adrenals and in brain then in liver. WT mice were IV injected with nanoparticle F12511 (30 mM DSPE-PEG, 6 mM phosphatidylcholine (PC), 12 mM F12511; 46 mg F12511/kg) or with vehicle and sacrificed after 4 hours. A1$^{-/-}$ refers to Acat1$^{-/-}$ mouse. Note, the major isoenzyme in mouse liver is ACAT2. ACAT activity was determined without or with perfusion as indicated. N=3-4 for WT mice age- and gender-matched. N=1 for A1$^{-/-}$ mouse. N.S., not significant; P<0.05*, P<0.01, P<0.001*. Two-way ANOVA. The significance is relative to vehicle-treated group.

F12511 encapsulated in DSPE-PEG$_{2000}$/PC nanoparticles (i.e., nanoparticle F12511) was also delivered to mice by IV. This analysis indicated that F12511 stayed in the blood at high level, entered the CNS, and inhibited ACAT in the brain significantly for a long time (longer than 8 hours). In particular, at 4 hours after IV injection, nanoparticle F12511 (at 46 mg nanoparticle F12511/kg) inhibited ACAT activity very effectively in the adrenals (by approx. 80%) and in the brain (by approx. 60-70%), but less effectively in the liver (40%)(FIG. 2). This analysis indicated that, when encapsulated in a nanoparticle, F12511 can avoid the liver on its first pass. As a component of the above-referenced analysis, a portion of the mice were treated with perfusion (to remove blood contamination from tissues). The results showed that there were no significant differences in ACAT inhibition between these two groups, indicating that the results of ACAT inhibition that were obtained were not due to the contamination of F12511 present in the blood.

The F12511 contents in the plasma and in various tissues were also analyzed by HPLC/MS/MS. The data presented in Table 6 demonstrated that at 4 hours after IV injection, the concentration of F12511 in the plasma was very high.

TABLE 6

| Delivery | Concentration of F12511 in Plasma | | Concentration of F12511 in Liver | | Concentration of F12511 in Brain | |
|---|---|---|---|---|---|---|
| | µM | ng/mL | µM | ng/mL | µM | ng/mL |
| Nanoparticle with F12511[1] | 48.4-58.4 | 22685-27391 | 2.3-6.8 | 1062-3210 | 0.07-0.08 | 32.5-39.3 |
| Nanoparticle with F12511 *Perfused*[1] | 23.9-66.6 | 11185-31224 | 1.5-4.3 | 702-2026 | 0.01-0.02 | 5.6-9.5 |
| DSPE-PEG/PC Nanoparticles[1] | 0 | 0 | 0 | 0 | 0 | 0 |
| F12511/ Cyclodextrin complex[2] | 0.75 | ~350 | NR | NR | NR | NR |

[1]n = 2 mice
[2]Reported in U.S. Pat. No. 6,864,246 B2 at peak of 2 hours.
NA, not reported For comparison, the concentration of F12511 in the plasma was at least 60-fold higher than the F12511 concentration in the plasma at 2 hours after oral feeding of F12511/Cyclodextrin complex to rats (see FIG. 11 of U.S. Pat. No. 6,864,246 B2). Using the method described here, the presence of F12511 in the brain was clearly detectable by HPLC/MS/MS. Note that the analysis was done after perfusion, thus ruling out the possibility that the observed presence of F12511 in the brain was due to blood contamination.

Example 9: ACAT1 Inhibition Suppresses Pro-Inflammatory Gene Expression

Figure 3A:
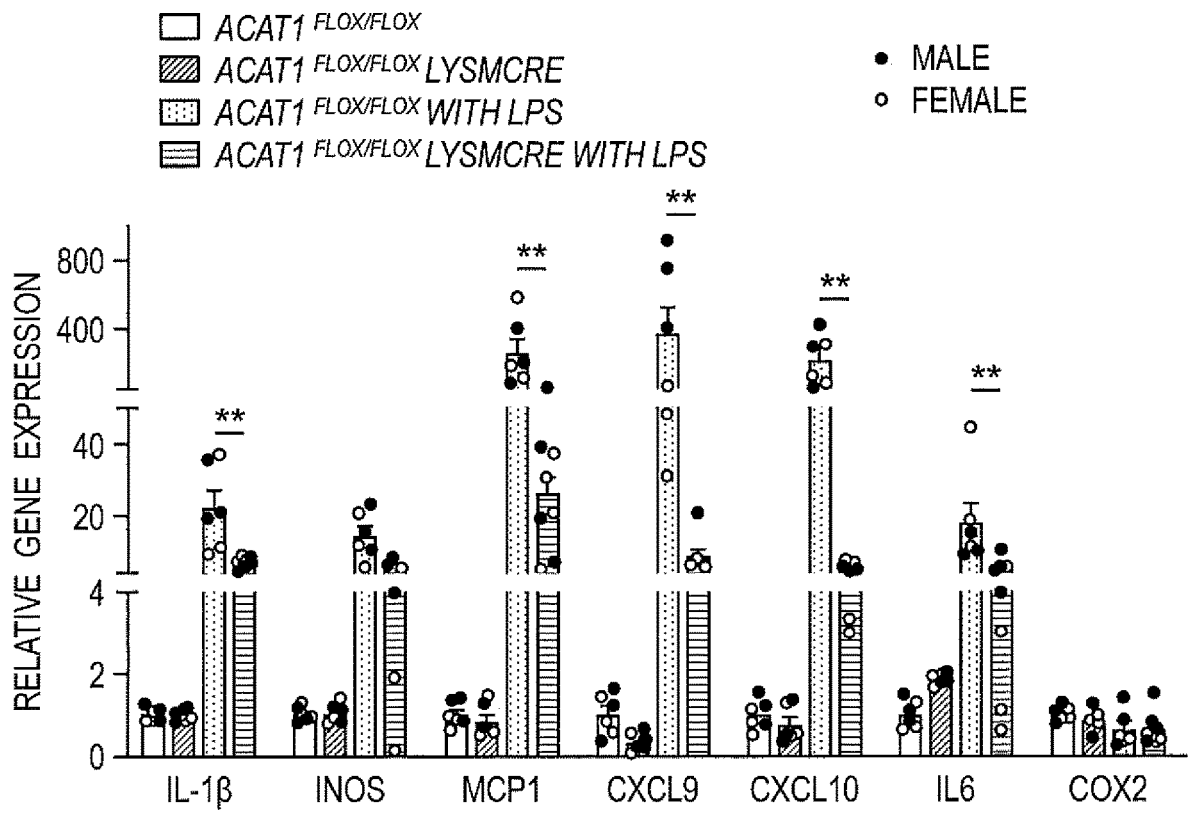
FIG. 3A-3D show that myeloid Acat1 inactivation suppresses expression of certain pro-inflammatory genes while inducing expression of certain anti-inflammatory genes after LPS injection to mice. Two-month-old Acat1$^{flox/flox}$ or Acat1$^{flox/flox}$ LyzM$^{Cre}$ (myeloid Acat1 knockout) mice were treated with single peritoneal injections of LPS at 5 mg/kg body weight. 24 hours later, mice were sacrificed, mRNA was extracted from hippocampus (FIGS. 3A and 3B) and cortex (FIGS. 3C and 3D) for qPCR to monitor expression of various pro-inflammatory genes (FIGS. 3A and 3C) or anti-inflammatory genes (FIGS. 3B and 3D). * P<0.05;  P<0.01; * P<0.001.
Figure 3B:
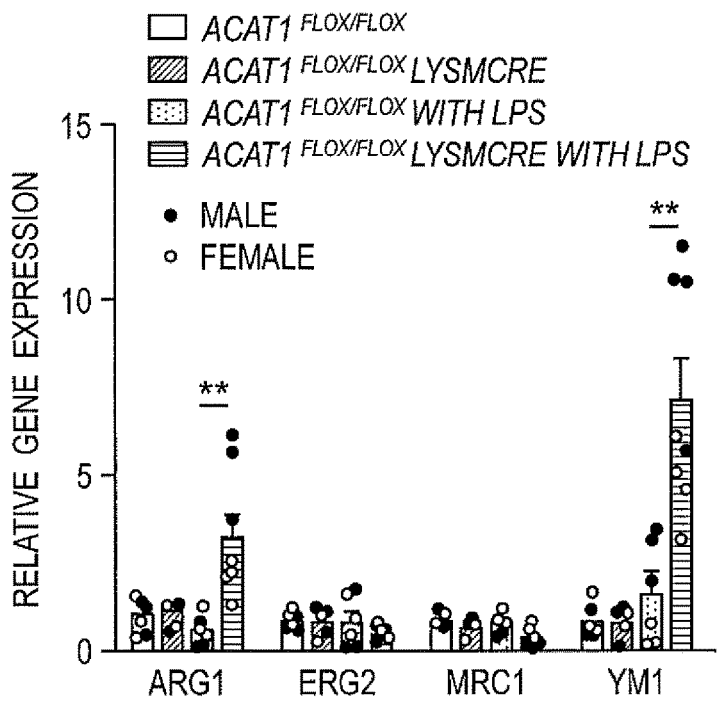
Figure 3C:
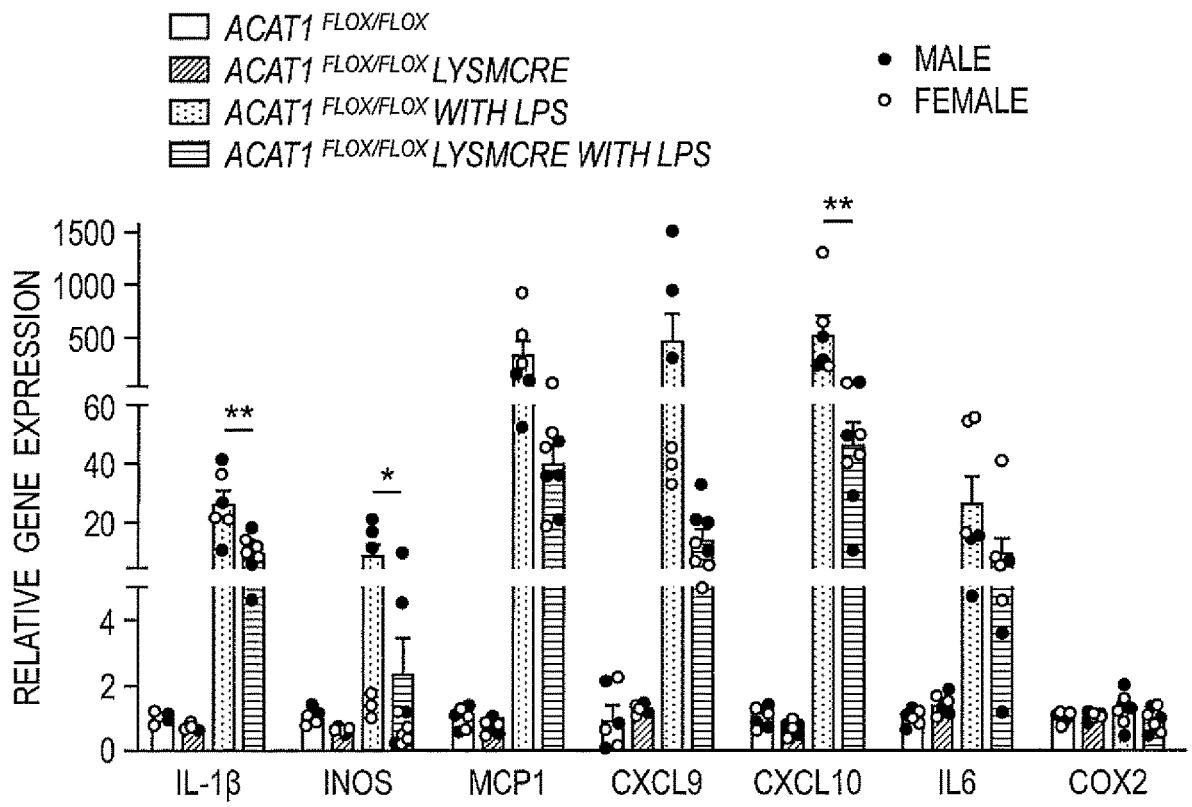
Figure 3D:
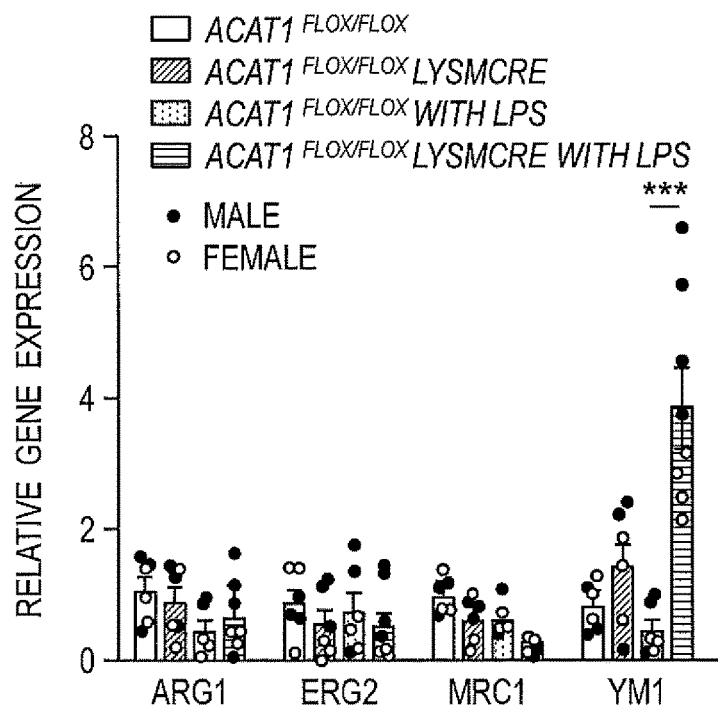
Figure 4A:
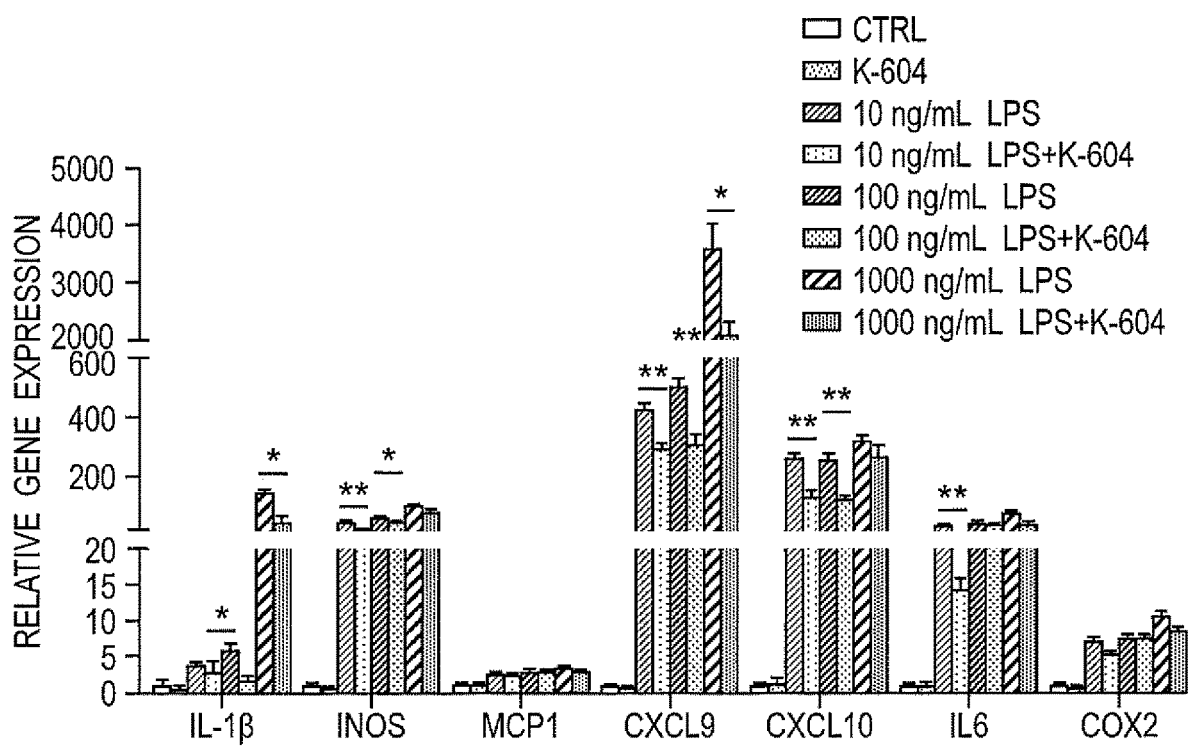

It has now been shown that, in microglia, genetic inactivation of Acat1 suppresses certain pro-inflammatory response genes (FIG. 3A and FIG. 3C, e.g., IL-1p, iNOS, MCP1, Cxcl9, Cxcl10 and IL-6) and induces certain anti-inflammatory response genes (FIG. 3B and FIG. 3D, e.g., YM1) in the hippocampus (FIG. 3A and FIG. 3B) and cortex (FIG. 3C and FIG. 3D). Likewise, inhibiting ACAT1 protein activity in microglial cells attenuates inflammatory responses to LPS (FIG. 4A-4C). These results indicate that the actions of ACAT1 blockage in microglia involves interleukin 4 (IL-4), which is one of the major anti-inflammatory cytokines. To demonstrate this in microglia, ACAT1 inhibition was shown to increase the protein content of IL4R-α, which is the receptor for IL-4 (FIG. 5).

In microglia, LPS uses Toll-like receptor 4 (TLR4) as one of the main receptors to mediate its inflammatory actions. The lipid efflux protein, ABCA1, is known to suppress pro-inflammatory responses, in part by attenuating the activity of TLR4 at the plasma membrane. Accordingly, it was posited that lipopolysaccharides (LPS) or other TLR4 agonists stimulate the CD36/TLR4-associated complexes at the plasma membrane (PM) and activate the cytosolic IkB kinase, which rapidly phosphorylates IkB (FIG. 4C), leading to its translocation from the cytosol into the nucleus to activate pro-inflammatory gene transcription. IL-4 or IL-13 binds to IL4Rα at the PM, which leads to the rapid phosphorylation of the transcription factor, STAT6, as well as increased expression of other transcription factors, including PPARγ and KLF4. These events increase the expression of anti-inflammatory genes. The ACAT1 blockade leads to accumulation of free cholesterol [and/or regulatory sterols such as 25-hydeoxycholesterol (25HC)], which further leads to an upregulation of IL4Rα to increase the anti-inflammatory cascade, and/or upregulation of ABCA1, and/or down-regulation of TLR4, to suppress the pro-inflammatory cascade.

Figure 6A:
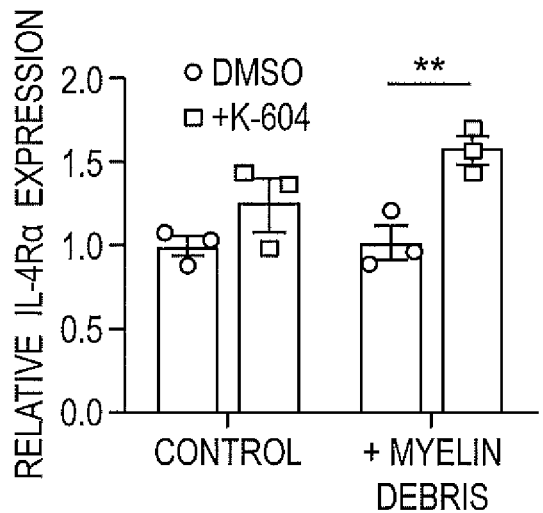
FIG. 6A-6B show that ACAT1 blockade upregulates IL-4Rα expression in mouse myelin debris-treated N9 (FIG. 6A) and HMC3 (FIG. 6B) microglia. Cells were grown until 90% confluency and subsequently treated with DMSO without or with K-604, or with myelin debris (purified as described by Rolfe, et al. (2017) J. Vis. Exp. 130:56322) for 21 hours. IL-4Rα expression was determined by convention methods. 25 µg/mL cholesterol equals 38 µg/mL total myelin debris protein. Data are expressed as mean±SEM. *P<0.05; **P<0.01.
Figure 6B:
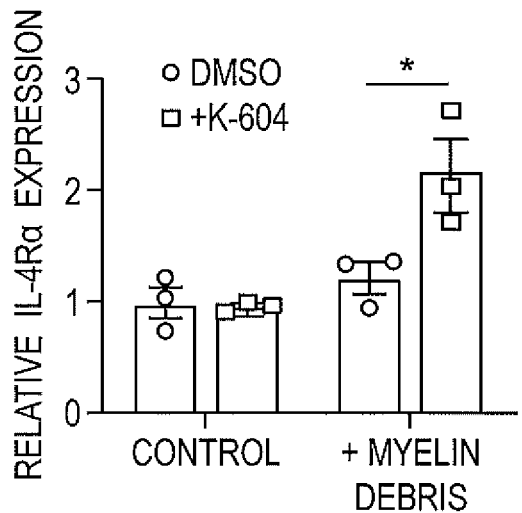

In microglia, various cholesterol-rich agents including myelin debris and damaged cell membranes enter the cells. It was posited that ACAT1 enzyme activity may be upregulated by cholesterol released from these cholesterol-rich agents. Accordingly, N9 cells were treated with myelin debris at two different doses (25 µg cholesterol/mL and 125 µg cholesterol/mL) for 21 hours and it was found that, indeed, myelin debris caused a significant increase in cholesterol ester biosynthesis, in a dose-dependent manner. To demonstrate the specificity of myelin debris in activating cholesteryl ester biosynthesis, N9 cells, when treated with myelin debris, did not exhibit any significant changes in triacylglycerol (TAG) biosynthesis or in phospholipid biosynthesis. In addition, the effects of ACAT1 blockade were tested in N9 and the human microglia-like cell line HMC3, which both express normal TREM-2 receptors. The results showed that, in both N9 cells (FIG. 6A) and HMC3 cells (FIG. 6B), the enhancing effect of ACAT1 inhibition by K-604 on IL4R-α was indeed more robust when cells were incubated with myelin debris in the media.

Figure 7A:
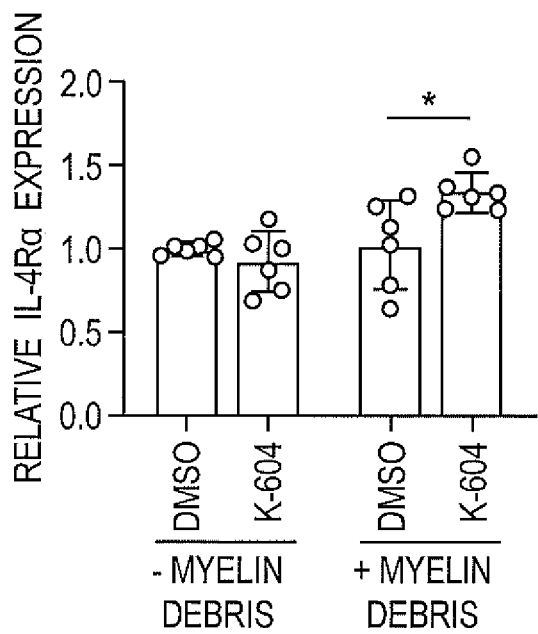
FIG. 7A-7B show that IL-4Rα protein content increases in human myelin debris-treated HMC3 cells after 48 hours co-incubation with either K-604 (FIG. 7A) or F12511 (FIG. 7B). Cells were grown until 90% confluency and subsequently treated with DMSO without or with ACAT inhibitor, with or without myelin debris for 21 hours. Protein was isolated and analyzed by western blot analysis. Vinculin was the loading control. Values were calculated based on the value with no myelin and K-604 or F12511 treatment as 1. Data are expressed as mean±SEM. *P<0.05; **P<0.01.
Figure 7B:
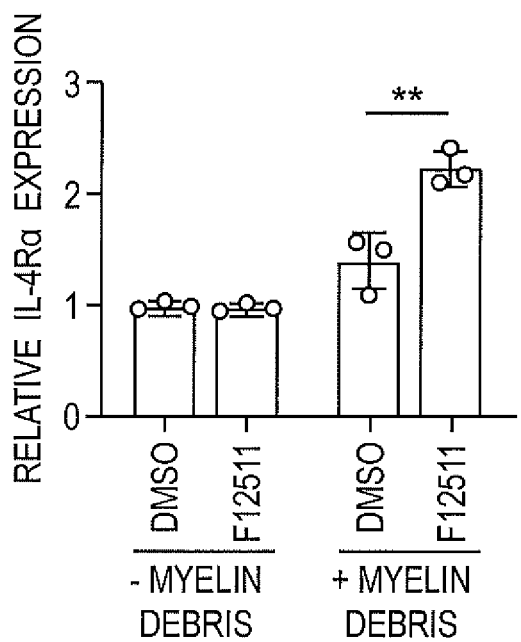
Figure 8A:
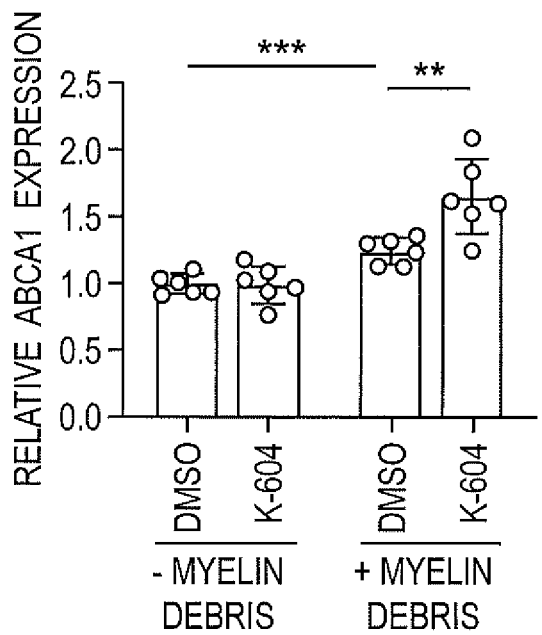
FIG. 8A-8B show that ABCA1 protein content increases in human myelin debris-treated HMC3 cells after 24 hours co-incubation with either K-604 or 12511 as the ACAT inhibitor. HMC3 cells were grown in MEM plus 10% BCS, with 0.1% DMSO as the control, or 0.5 µM K-604 (FIG. 8A) or 0.5 µM F12511 incubated with or without human myelin debris at 25 µg/mL cholesterol for 24 hours. Afterward, cells were harvested for western blot analyses. Lysates of HEK293 cells and lysates of HMC3 cells treated with 10 µM LXR agonist T0901317 for 24 hours were respectively used as negative and positive controls for ABCA1 signals. Values were based on the value of lysates from cells with no myelin or K-604 or F12511 treatments as 1. Data are expressed as mean±SEM.
Figure 8B:
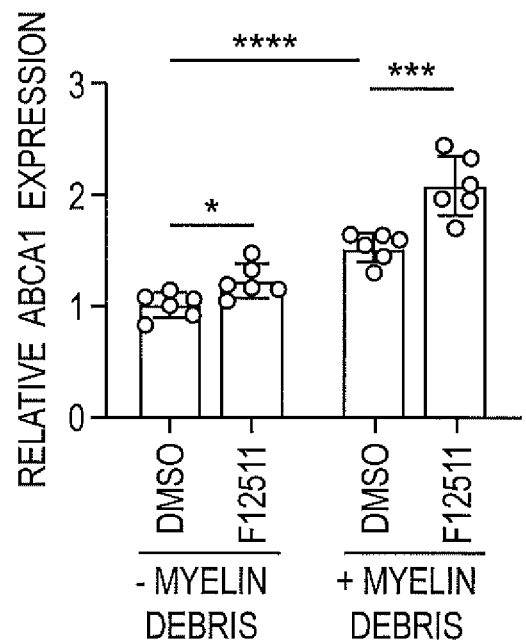

Subsequently, myelin debris from human brains was prepared and it was observed that the cholesterol/protein ratio, as well as the protein composition between mouse myelin debris and human myelin debris, were very similar. In N9 cells, human myelin debris added to the medium at 25 µg/mL cholesterol also significantly increased cholesteryl ester biosynthesis; this synthesis was effectively suppressed by ACAT1 inhibitor K-604. In HMC3 cells, the enhancing effects of K-604 on IL4R-α levels (FIG. 7A) was replicated by F12511 (FIG. 7B). It was also found that the protein content of the key lipid efflux protein, ABCA1 increased significantly in human myelin debris-treated HMC3 after cells were co-incubated with either K-604 (FIG. 8A) or F12511 (FIG. 8B) as the ACAT inhibitor for 24 hours. A similar effect was observed with N9 cells. In summary, the enhancing effects of myelin debris on cholesteryl ester biosynthesis were observed in mouse and human microglial cell lines. Further, the enhancing effects of ACAT1 inhibition on IL4R-α and ABCA1 protein levels in myelin debris-treated HMC3 cells and N9 cells was observed using two different ACAT inhibitors, K-604 and F12511.

Example 10: F12511 Analog, F26, is a Brain Permeable ACAT Inhibitor

ACAT1 has now been shown to be a drug target for the treatment of AD. To achieve optimal drug development and treatment, it is important to develop potent brain-permeable ACAT inhibitors. In this regard, a close analog of F12511 has been described, F26 (US 2006/0135785), which differs from F12511 by having a sulfonyl moiety at the carbon adjacent to the asymmetric carbon. In addition, the asymmetric carbon contains a fluorine moiety (see Table 2). The $IC_{50}$ values of F12511 and F26 (98% pure) for human ACAT1 were compared using the mixed liposome assay and the results indicated that F26 was almost 3 times more potent than F12511 as an ACAT inhibitor (F12511 $IC_{50}$=37 nM, F26 $IC_{50}$=13 nM).

Figure 9:
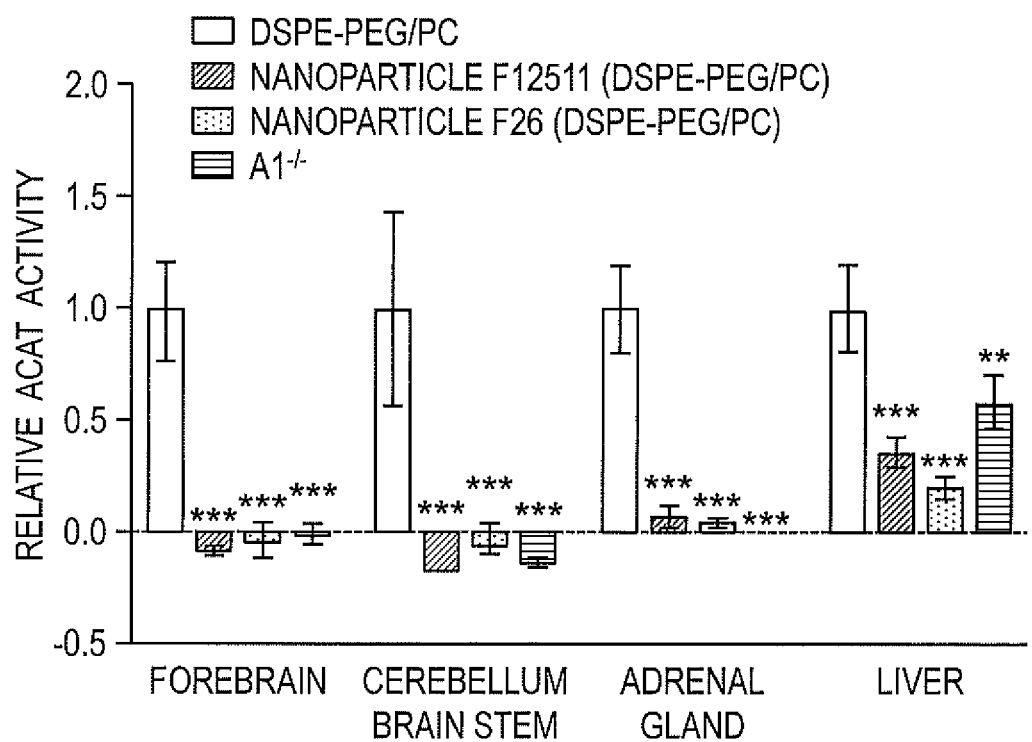
FIG. 9 shows that IV injection of nanoparticle F12511 and nanoparticle F26 (10 mL/kg, ~46 mg/kg) reduces ACAT activities in both adrenal glands and the brain after 4 hours. Mice were perfused before brains were isolated. N=2-3 WT mice/group. N=1 A1$^{-/-}$ mouse. Statistical analysis, 2-way ANOVA. *P<0.05; P<0.01; *P<0.001.

To determine in vivo activity, F12511 and F26 were delivered IV to mice via stealth nanoparticles (nanoparticle F12511 and nanoparticle F26), both at relatively high concentration (46 mg/kg). The results indicated that 4 hours after IV injection, both F12511 and F26 very effectively inhibited ACAT enzyme activity (by more than 80-90%) in the brain and in the adrenal glands (FIG. 9). This analysis further demonstrated that both F12511 and F26 are high-affinity ACAT inhibitors and both are brain permeable.

Example 11: Tissue Distribution and Adrenal Toxicity Studies of F12511

It was determined whether nanoparticle F12511 could continue to suppress ACAT in the brain after repeated injections. In this study, mice were injected with 46 mg nanoparticle F12511/kg IV through the retro-orbital sinus once every other day for 14 days. The results showed that 6 hours after the last injection, nanoparticle F12511 inhibited ACAT activity in the brain by at least 60-70%.

Figures 10A, 10B, 10C, 10D:
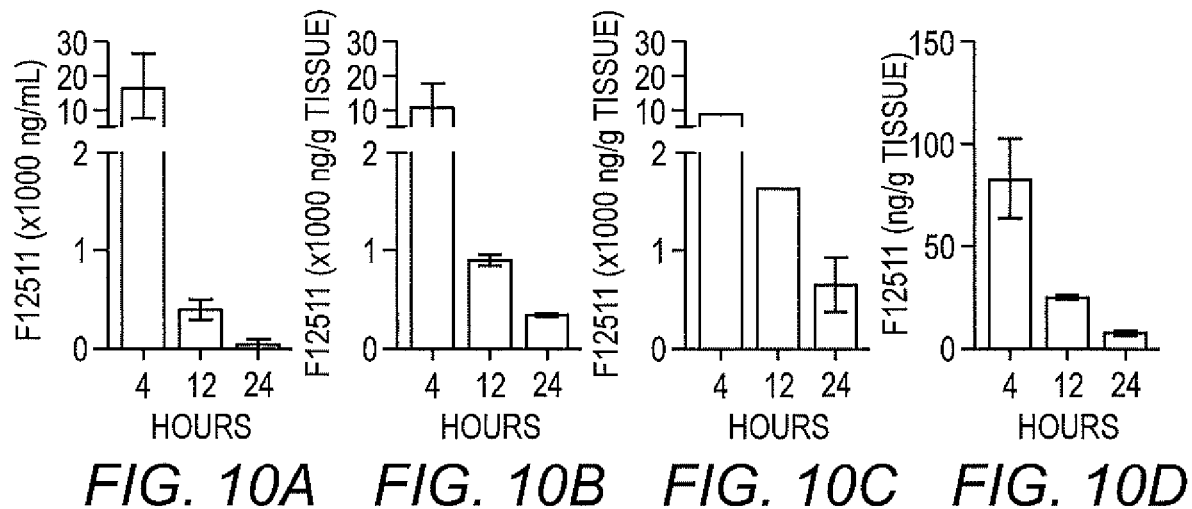
FIG. 10A-10D show that rapid decline of F12511 content occurs over time in plasma (FIG. 10A), liver (FIG. 10B), adrenals (FIG. 10C), and brain (FIG. 10D) after a single IV Injection of nanoparticle F12511 at high concentration (46 mg/kg). The F12511 content in various tissues was determined by HPLC/MS/MS. N=4 for the 4-hour time point and N=2 for the 12- and 24-hour time points.

Subsequently, it was determined whether nanoparticle F12511 caused adrenal toxicities in mice. When fed to mice for seven days, certain toxic ACAT inhibitors, such as AZD3988 cause significant reduction in fine vacuolation in various cortical regions. Therefore, it was determined whether prolonged injections of nanoparticle F12511 may produce adrenal toxicity. Nanoparticle F12511 was administered through tail vein via IV injection at 46 mg F12511/kg once per day to mice for 7 consecutive days. Two days after the last injection, the mice were sacrificed and the morphology of various regions of the adrenal cortices was examined after histochemical staining. The results showed that, when compared to untreated mice, neither nanoparticle F12511 nor control nanoparticle produced detectable reduction in cortical vacuolation nor degeneration/necrosis in the adrenal cortex Adrenal toxicity of certain toxic ACAT inhibitors such as ATR101 is, in part, caused by preferential accumulation within the adrenal glands at high concentrations. To test if IV injection of nanoparticle F12511 causes preferential accumulation in adrenals, LC/MS/MS analyses of tissues (Mesplet, et al. (2005) Rapid Comm. Mass Spec. 19:297-302) were conducted after IV injection of nanoparticle F12511. For these analyses, the quantitative range for F12511 was 0.3-1000 ng/mL for liver, brain, and whole blood. The results (FIG. 7A-7D) showed that after a single IV injection of nanoparticle F12511, at high dose (46 mg F12511/kg), the F12511 content was very high at 4 hours after IV injection, achieving a concentration in the blood of 10 microgram/ml (21 microM), and decreased rapidly in the plasma (FIG. 10A), adrenals (FIG. 10C), livers (FIG. 10B), and brains (FIG. 10D); there was no evidence for preferential accumulation of F12511 in the adrenals. Further, this analysis demonstrated that about 10% of F12511 in the blood enters the liver and adrenals and about 1% of F12511 in the blood enters the brain.

Figure 11:
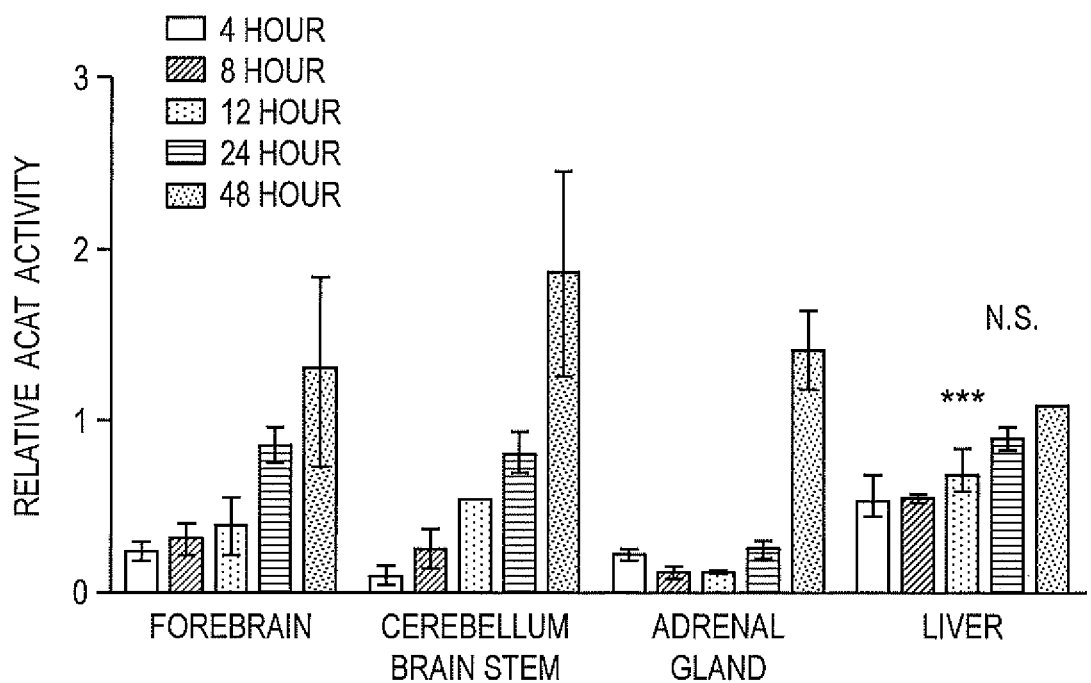
FIG. 11 shows that ACAT activity in forebrain, cerebellum brain stem, adrenal gland, and liver tissues steadily returns to normal levels after a single IV injection of nanoparticle F12511 at high concentration (46 mg/kg). Two WT mice per each time point; ACAT enzyme assay in triplicate.

ACAT enzyme activities in various tissues at 4-48 hours after a single IV injection of nanoparticle F12511 at 46 mg/kg was also monitored. The results showed that the ACAT enzyme activity in various tissues (including the adrenal glands) steadily returned to near-normal levels within 24-48 hours (FIG. 11). Notably, while 1% of F12511 in the blood enters the brain, this level of F12511 in the brain is sufficient to inhibit ACAT1 in the brain. These results indicated that the inhibition of ACAT activity by nanoparticle F12511 was reversible, and that there was no evidence to suggest prolonged, preferential accumulation of F12511 in the adrenals. Overall, these results demonstrate that nanoparticle F12511, when delivered at high concentrations, produces no obvious toxicities in cell culture or in viva.

Figure 12:
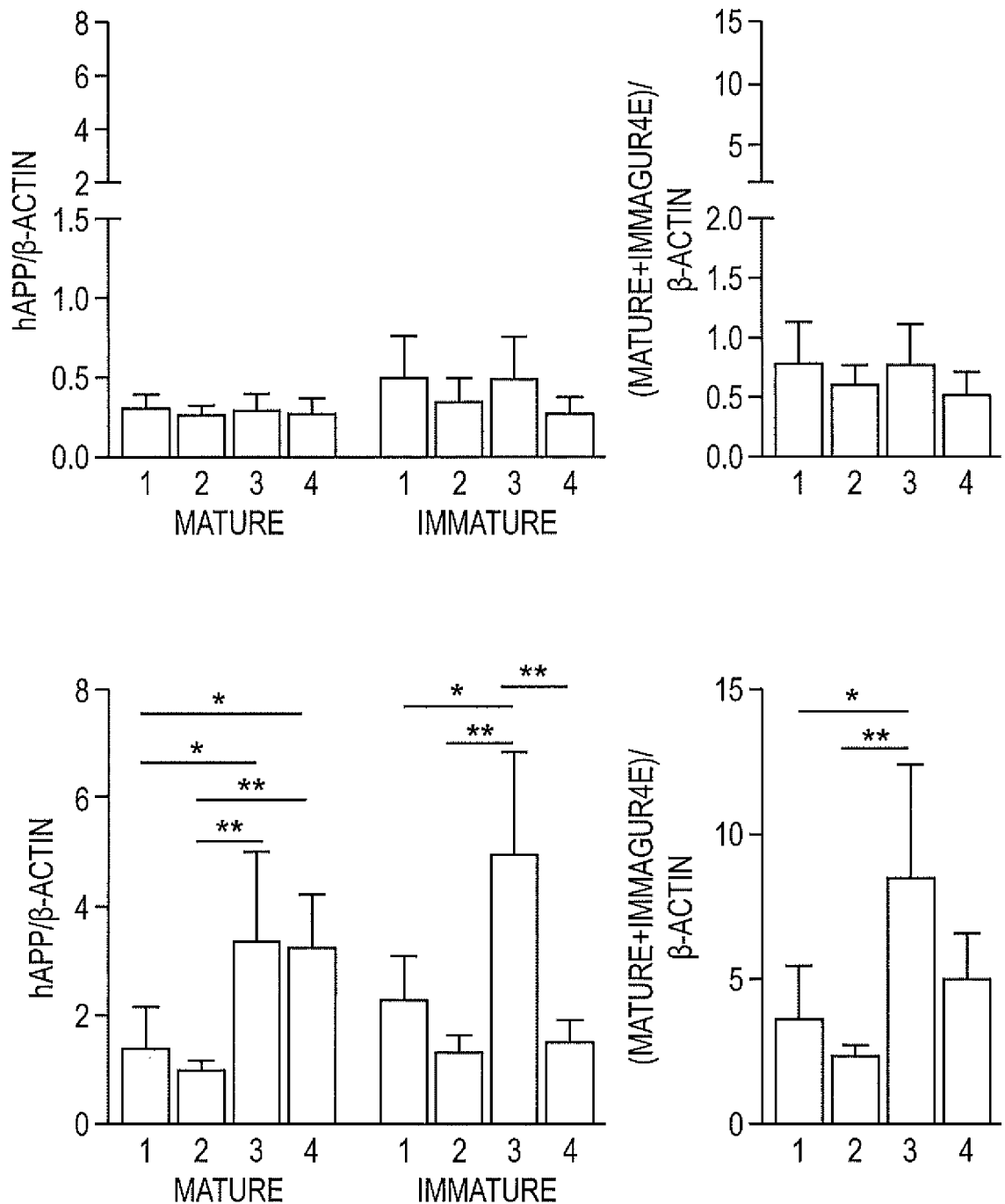
FIG. 12 shows that amyloid pathology is reduced after treatment with either Nanoparticle alone or Nanoparticle F in advance-age mice, with Nanoparticle F being more efficient than Nanoparticle alone. 3xTg-AD mice were treated with either DSPE-PEG$_{2000}$/PC (Nanoparticle alone with 30 mM DSPE-PEG and 6 mM PC) or Nanoparticle F (with 30 mM DSPE-PEG, 6 mM PC and 10 mM F) and compared to PBS treated or untreated mice as indicated, as well as to untreated 3xTg-AD Acat1$^{-/-}$ mice. Mice were grouped into middle (6-8 months old), or advanced (16-20 months old,) ages and treated for 1 week (middle) or for 2 weeks (advanced) with daily i.v. injections. Western blot analyses were conducted using mouse anti-6e10 antibody (that recognizes β-amyloid fragment 1-42) and mouse anti-β-actin antibodies. Two-way ANOVA was conducted for hAPP results in advanced (16-20 months old) and middle (6-8 months old) aged mice. hAPP was separated via SDS-PAGE into two adjacent bands, i.e., the mature and immature forms, both of which are recognized by the anti-6e10 antibody (Bryleva et al. (2010) Proc. Natl. Acad. Sci. USA 107(7):3081-6). One-way ANOVA was done for total signal ("mature+immature" hAPP results). Results are average of three readings from the same blot. (1) DSPE-PEG/PC Nanoparticle alone; (2) Nanoparticle F; (3) 3xTg-AD Acat1$^{+/+}$ (PBS or untreated); (4) 3xTg-AD Acat1$^{-/-}$ (untreated). **, p<0.01; *, p<0.05.

Example 12: Amyloid and Tau Pathology Studies of Nanoparticle F12511 and Nanoparticle Alone 3xTg-AD mice were treated with either DSPE-PEG$_{2000}$/PC (Nanoparticle alone) or Nanoparticle F and compared to PBS treated or untreated mice, as well as to untreated 3xTg-AD Acat1$^{-/-}$ mice. Mice were grouped into middle (6-8 months old), or advanced (16-20 months old) ages and treated for 1 week (middle) or for 2 weeks (advanced) with daily i.v. injections of Nanoparticle alone, Nanoparticle F or PBS. Proteins were extracted, separated by SDS-PAGE and analyzed via western blot analysis using mouse anti-6e10 antibody, which recognizes β-amyloid fragment 1-42 and mouse anti-beta actin antibodies (control). Results from this analysis showed that in advance-aged mice, both Nanoparticle alone and Nanoparticle F reduced amyloid pathology, with Nanoparticle alone being less efficient than Nanoparticle F (FIG. 12, bottom panel). For comparison, the middle age group received treatment for 1 week only; neither nanoparticle F nor nanoparticle alone reduced amyloid pathology (FIG. 12, top panel).

Figure 13:
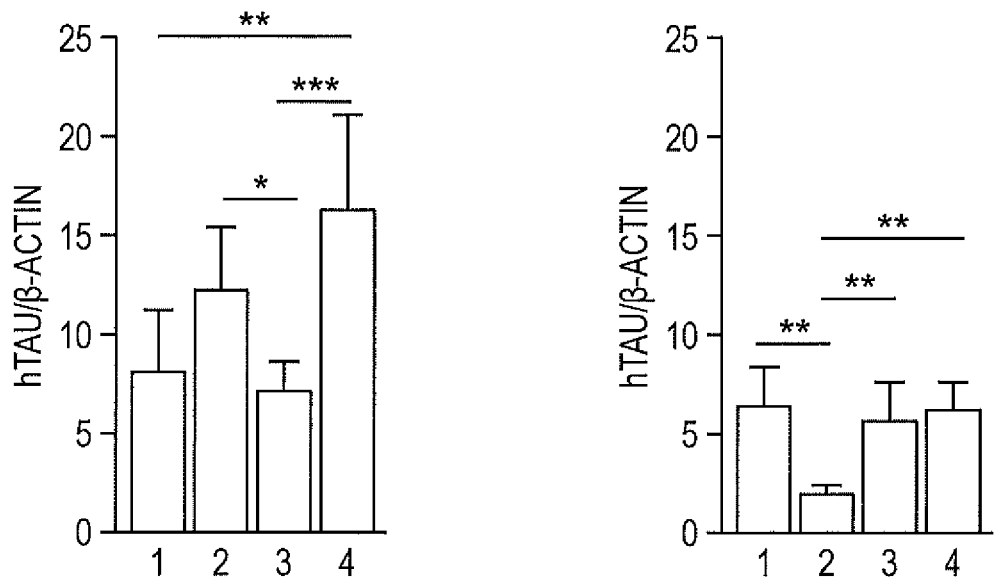
FIG. 13 shows that in advanced 3xTg-AD mice (16-20 months), Nanoparticle F but not Nanoparticle alone reduces the monomeric human tau levels. 3xTg-AD mice were treated as described in FIG. 12. Western blot analyses were conducted using mouse anti-HT7 antibody (which recognizes the human monomeric tau at 50 kDa in SDS-PAGE), and mouse anti-β-actin antibodies. One-way ANOVA was conducted to determine significance levels. Results are average of three readings from the same blot. (1) DSPE-PEG/PC Nanoparticle alone; (2) Nanoparticle F; (3) 3xTg-AD Acat1$^{+/+}$ (PBS or untreated); (4) 3xTg-AD Acat1$^{-/-}$ (untreated). *, p<0.001; , p<0.01; *, p<0.05.

Similar studies were conducted to measure htau. 3xTg-AD mice were treated as described above. Western blot analyses were conducted using mouse anti-HT7 antibody (which recognizes the human monomeric tau 50 kDa in SDS-PAGE), mouse anti-AT8 (which recognizes aggregated and hyperphosphorylated human tau at 55-60 kDa in SDS-PAGE) and mouse anti-beta actin antibodies. Results from this analysis showed that in advanced 3xTg-AD mice, Nanoparticle F, but not Nanoparticle alone, reduces monomeric human tau levels (FIG. 13, right panel). By comparison, in middle age 3xTg-AD mice that received treatment for 1 week only, neither nanoparticle F nor nanoparticle alone reduced human tau (FIG. 13, left panel).

Figure 14:
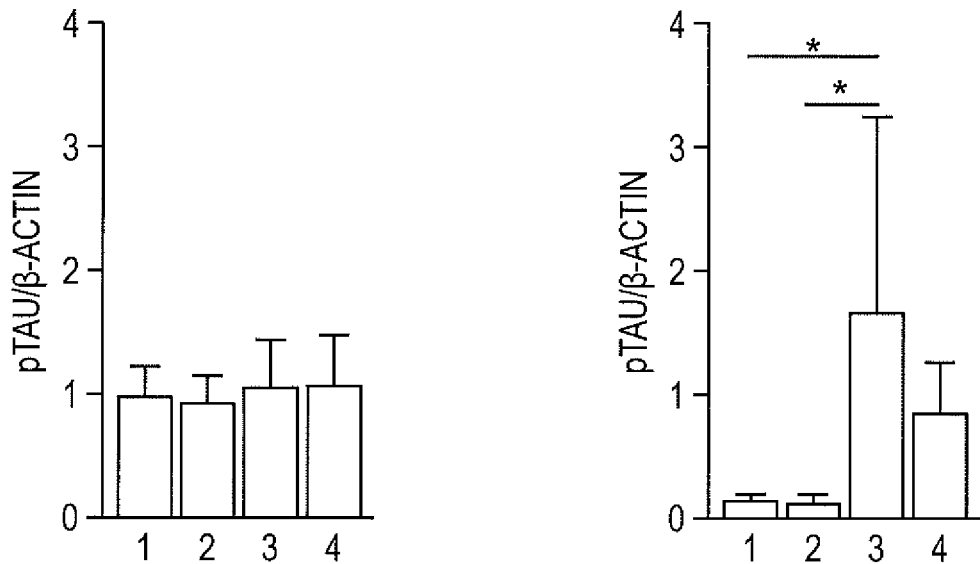
FIG. 14 shows that treatment with either Nanoparticle alone or with nanoparticle F for 2 weeks reduces aggregated and hyperphosphorylated tau levels. 3xTg-AD mice were treated as described in FIG. 12. Western blot analyses were conducted using mouse anti-ATB (which recognizes aggregated and hyperphosphorylated human tau at 55-60 kDa in SDS-PAGE) and mouse anti-β-actin antibodies. One-way ANOVA was conducted to determine significance levels. Results are average of three readings from the same blot. (1) DSPE-PEG/PC Nanoparticle alone; (2) Nanoparticle F; (3) 3xTg-AD Acat1$^{+/+}$ (PBS or untreated); (4) 3xTg-AD Acat1$^{-/-}$ (untreated). *, p<0.05.

In advanced 3xTg-AD mice, treatment with either Nanoparticle alone or with Nanoparticle F for 2 weeks reduced aggregated and hyperphosphorylated htau levels (FIG. 14, right panel). By comparison, in middle age 3xTg-AD mice, treatment with either Nanoparticle alone or with Nanoparticle F for 1 week only was not able to reduce aggregated and hyperphosphorylated tau levels (FIG. 14, left panel).

Overall, these results show that in the advanced age group, either Nanoparticle alone or Nanoparticle F (treatment for 2 weeks) reduced amyloid pathology, with Nanoparticle F being more efficient than Nanoparticle alone. In addition, Nanoparticle F, but not Nanoparticle alone reduced the total non-aggregated, monomeric tau. Moreover, either Nanoparticle alone or Nanoparticle F (treatment for 2 weeks) reduced aggregated and hyperphosphorylated tau levels. By comparison, in the middle age group, the treatment was for 1 week only, and the results show that neither Nanoparticle alone nor with Nanoparticle F was as effective in reducing amyloid pathology or in reducing aggregated and hyperphosphorylated tau levels. Therefore, Nanoparticle F provides a multi-potent therapeutic for reducing neuroinflammation, reducing amyloidopathy and reducing tauopathy in aging, symptomatic Alzheimer's disease. In addition, Nanoparticle alone also provides a multi-potent therapeutic for reducing amyloidopathy and reducing tauopathy in aging, symptomatic Alzheimer's disease.

What is claimed is:

1. Nanoparticles for reducing or attenuating neuroinflammation, amyloidopathy or tauopathy comprising a core and an outer lipid envelope, the core comprising an Acyl-CoA:Cholesterol Acyltransferase (ACAT) inhibitor and the outer lipid envelope comprising distearoyl-sn-glycero-3-phosphoethanolamine-poly(ethylene glycol) and phosphatidylcholine, wherein the concentration of phosphatidylcholine is greater than or equal to 6 mM and the ratio of ACAT inhibitor to phosphatidylcholine is in the range of about 0.3:1 to 2:1.

2. The nanoparticles of claim 1, wherein the ACAT inhibitor is F12511 or an analog thereof.

3. The nanoparticles of claim 2, wherein the analog has the structure:

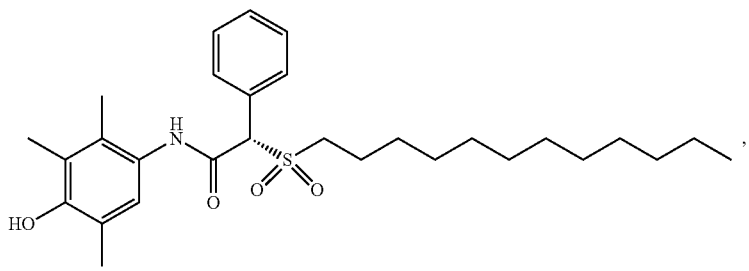

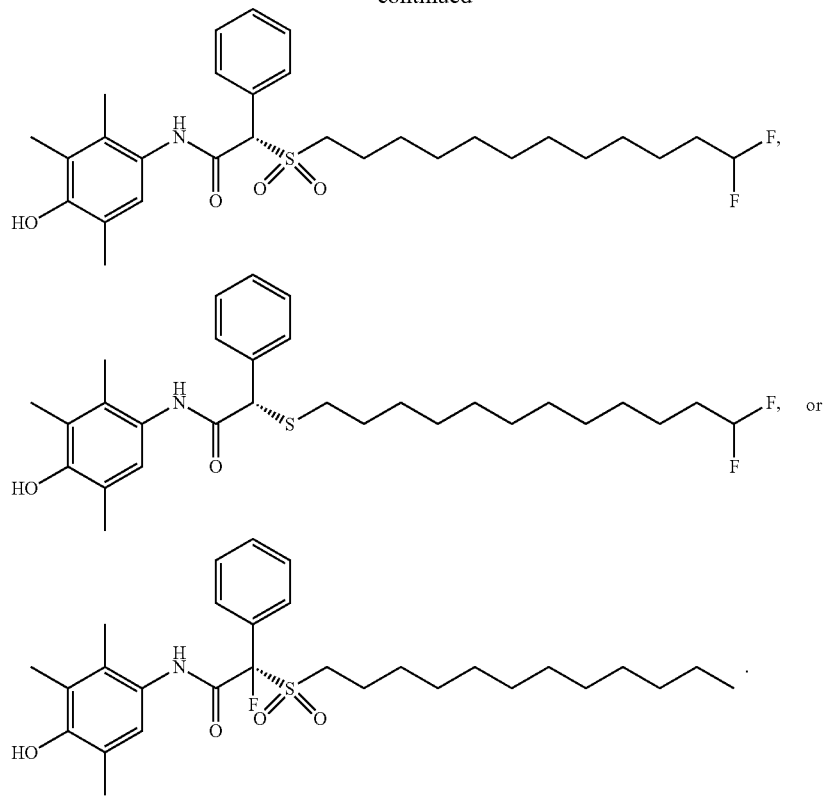

4. A pharmaceutical composition comprising nanoparticles in admixture with a pharmaceutically acceptable carrier, the nanoparticles comprising a core and an outer lipid envelope, the core comprising an Acyl-CoA:Cholesterol Acyltransferase (ACAT) inhibitor and the outer lipid envelope comprising disteraoyl-3-phosphoethanolamine-poly(ethylene glycol) and phosphatidylcholine, wherein the concentration of phosphatidylcholine is greater than or equal to 6 mM and said pharmaceutical composition is formulated for intravenous or intraperitoneal delivery.

5. A pharmaceutical composition comprising the nanoparticles of claim 1 in admixture with a pharmaceutically acceptable carrier.

6. The pharmaceutical composition of claim 5, wherein said pharmaceutical composition is formulated for intravenous or intraperitoneal delivery.

* * * * *